United States Patent
Lam et al.

(10) Patent No.: US 9,309,561 B2
(45) Date of Patent: Apr. 12, 2016

(54) METHODS AND KITS USING EXTENDED RHODAMINE DYES

(71) Applicant: APPLIED BIOSYSTEMS, LLC, Carlsbad, CA (US)

(72) Inventors: Joe Y. L. Lam, Castro Valley, CA (US); Scott C. Benson, Alameda, CA (US); Steven M. Menchen, Fremont, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 85 days.

(21) Appl. No.: 14/098,519

(22) Filed: Dec. 5, 2013

(65) Prior Publication Data
US 2014/0171336 A1 Jun. 19, 2014

Related U.S. Application Data

(60) Continuation of application No. 13/365,554, filed on Feb. 3, 2012, now Pat. No. 8,628,975, which is a continuation of application No. 12/846,773, filed on Jul. 29, 2010, now Pat. No. 8,124,746, which is a division of application No. 10/925,411, filed on Aug. 24, 2004, now Pat. No. 7,776,568, which is a division of application No. 09/780,600, filed on Feb. 9, 2001, now Pat. No. 6,781,001, which is a division of application No. 09/325,243, filed on Jun. 3, 1999, now Pat. No. 6,248,884.

(51) Int. Cl.

| | |
|---|---|
| *C12Q 1/68* | (2006.01) |
| *C07D 209/60* | (2006.01) |
| *C07D 221/08* | (2006.01) |
| *C07D 221/10* | (2006.01) |
| *C07D 471/06* | (2006.01) |
| *C07D 487/06* | (2006.01) |
| *C07D 491/14* | (2006.01) |
| *C07H 19/04* | (2006.01) |
| *C07H 21/00* | (2006.01) |
| *C09B 11/24* | (2006.01) |

(52) U.S. Cl.
CPC ............ *C12Q 1/6816* (2013.01); *C07D 209/60* (2013.01); *C07D 221/08* (2013.01); *C07D 221/10* (2013.01); *C07D 471/06* (2013.01); *C07D 487/06* (2013.01); *C07D 491/14* (2013.01); *C07H 19/04* (2013.01); *C07H 21/00* (2013.01); *C09B 11/24* (2013.01); *C12Q 1/68* (2013.01); *Y10S 435/968* (2013.01); *Y10S 435/975* (2013.01); *Y10S 436/80* (2013.01); *Y10T 436/143333* (2015.01)

(58) Field of Classification Search
CPC ........................................................ C12Q 1/68
USPC ........................................................ 435/6.1
See application file for complete search history.

(56) References Cited

U.S. PATENT DOCUMENTS

| | | |
|---|---|---|
| 3,694,462 A | 9/1972 | Grisdale |
| 3,745,176 A | 7/1973 | Grisdale |

(Continued)

FOREIGN PATENT DOCUMENTS

| | | |
|---|---|---|
| DE | 223149 | 6/1985 |
| EP | 0543333 | 5/1993 |

(Continued)

OTHER PUBLICATIONS

EP00942657.8 Office Action mailed May 31, 2002.

(Continued)

*Primary Examiner* — Ardin Marschel
(74) *Attorney, Agent, or Firm* — Thompson Hine LLP

(57) ABSTRACT

Extended rhodamine compounds exhibiting favorable fluorescence characteristics having the structure

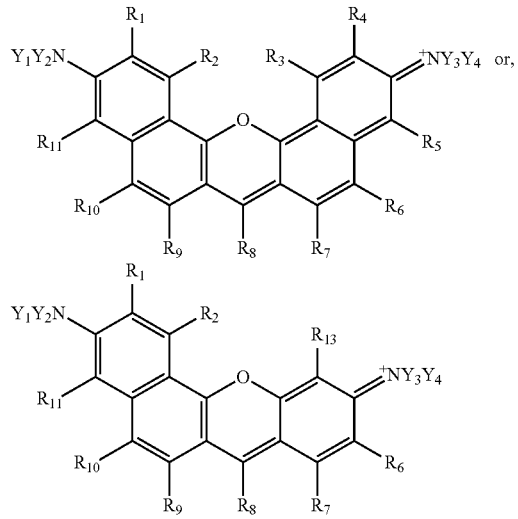

are disclosed. In addition, novel intermediates for synthesis of these dyes are disclosed, such intermediates having the structure

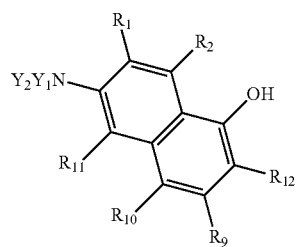

In addition, methods of making and using the dyes as fluorescent labels are disclosed.

12 Claims, No Drawings

(56) References Cited

U.S. PATENT DOCUMENTS

| | | | |
|---|---|---|---|
| 4,237,281 | A | 12/1980 | Long |
| 5,034,531 | A | 7/1991 | Friary et al. |
| 5,066,580 | A | 11/1991 | Lee |
| 5,776,931 | A | 7/1998 | Nunes et al. |
| 5,831,045 | A | 11/1998 | Stolowitz et al. |
| 5,847,162 | A | 12/1998 | Lee et al. |
| 6,111,116 | A | 8/2000 | Benson et al. |
| 6,248,884 | B1 | 6/2001 | Lam et al. |
| 6,781,001 | B2 * | 8/2004 | Lam et al. .................... 549/382 |
| 7,776,568 | B2 | 8/2010 | Lam et al. |
| 8,124,746 | B2 * | 2/2012 | Lam et al. .................... 536/22.1 |
| 8,628,975 | B2 * | 1/2014 | Lam et al. ....................... 436/94 |
| 2011/0053282 | A1 | 3/2011 | Lam et al. |

FOREIGN PATENT DOCUMENTS

| | | |
|---|---|---|
| EP | 0805190 | 11/1997 |
| WO | WO-0075236 | 12/2000 |

OTHER PUBLICATIONS

EP00942657.8 Office Action mailed Nov. 13, 2002.
EP04001709.7 Office Action mailed Nov. 19, 2004.
EP04001709.7, European Search Report mailed Mar. 18, 2004.
Kamel, Mohamed et al., "Zur Kenntnis der Dibenzoxanthyliumsalze II", *Helvetica Chimica Acta*, vol. 43, 1960, Jan. 18, 1960, 594-600.
Koresawa, Mitsunori et al., "Development of a Time-Resolved Flurometric Detection System Using Diffusion-Enhanced Energy Transfer", *Analytical Chemistry*, vol. 72, Oct. 15, 2000, 4904-4907.
PCT/US00/15085, International Preliminary Examination Report mailed Jul. 13, 2001.
PCT/US00/15085, International Search Report mailed Oct. 17, 2000.
PCT/US00/15085, Written Opinion mailed Mar. 7, 2001.
Zander, Maximilian et al., "Über Carbazolo-carbazole", *Chemische Berichte*, vol. 102, Feb. 21, 1969, 2728-2738.

* cited by examiner

METHODS AND KITS USING EXTENDED RHODAMINE DYES

CROSS-REFERENCE TO RELATED APPLICATIONS

This application is a Continuation of U.S. application Ser. No. 13/365,554, filed on Feb. 3, 2012, now U.S. Pat. No. 8,628,975, which is a Continuation of U.S. application Ser. No. 12/846,773, filed on Jul. 29, 2010, now U.S. Pat. No. 8,124,746, which is a Division of U.S. application Ser. No. 10/925,411, filed on Aug. 24, 2004, now U.S. Pat. No. 7,776,568, which is a Division of U.S. application Ser. No. 09/780,600, filed on Feb. 9, 2001, now U.S. Pat. No. 6,781,001, which is a Division of U.S. application No. 09/325,243, filed Jun. 3, 1999, now U.S. Pat. No. 6,248,884, each of which disclosures is herein incorporated by reference in its entirety.

FIELD OF THE INVENTION

This invention relates generally to fluorescent dye compounds. More specifically, this invention relates to extended rhodamine dyes useful as fluorescent labeling reagents.

BACKGROUND

The non-radioactive detection of biological analytes utilizing fluorescent labels is an important technology in modern molecular biology. By eliminating the need for radioactive labels, safety is enhance and the environmental impact and costs associated with reagent disposal is greatly reduced. Examples of methods utilizing such non-radioactive fluorescent detection include automated DNA sequencing, oligonucleotide hybridization methods, detection of polymerase-chain-reaction products, immunoassays, and the like.

In many applications it is advantageous to employ multiple spectrally distinguishable fluorescent labels in order to achieve independent detection of a plurality of spatially overlapping analytes, i.e., multiplex fluorescent detection. Examples of methods utilizing multiplex fluorescent detection include single-tube multiplex DNA probe assays and multi-color automated DNA sequencing. In the case of multiplex DNA probe assays, by employing multiplex fluorescent detection, the number of reaction tubes may be reduced thereby simplifying experimental protocols and facilitating the production of application-specific reagent kits. In the case of multi-color automated DNA sequencing, multiplex fluorescent detection allows for the analysis of multiple nucleotide bases in a single electrophoresis lane thereby increasing throughput over single-color methods and reducing uncertainties associated with inter-lane electrophoretic mobility variations.

Assembling a set of multiple spectrally distinguishable fluorescent labels useful for multiplex fluorescent detection is problematic. Multiplex fluorescent detection imposes at least six severe constraints on the selection of component fluorescent labels, particularly for applications requiring a single excitation light source, an electrophoretic separation, and/or treatment with enzymes, e.g., automated DNA sequencing. First, it is difficult to find a set of structurally similar dyes whose emission spectra are spectrally resolved, since the typical emission band half-width for organic fluorescent dyes is about 40-80 nanometers (nm). Second, even if dyes with non-overlapping emission spectra are identified, the set may still not be suitable if the respective fluorescent quantum efficiencies are too low. Third, when several fluorescent dyes are used concurrently, simultaneous excitation becomes difficult because the absorption bands of the dyes are usually widely separated. Fourth, the charge, molecular size, and conformation of the dyes must not adversely affect the electrophoretic mobilities of the analyte. Fifth, the fluorescent dyes must be compatible with the chemistry used to create or manipulate the analyte, e.g., DNA synthesis solvents and reagents, buffers, polymerase enzymes, ligase enzymes, and the like. Sixth, the dye must have sufficient photostability to withstand laser excitation.

Currently available multiplex dye sets suitable for use in four-color automated DNA sequencing applications require blue or blue-green laser light to adequately excite fluorescence emissions from all of the dyes making up the set, e.g., argon-ion lasers. Use of such lasers in commercial automated DNA sequencing systems is disadvantageous because of their high cost and limited lifetime.

Thus, there exists a need for fluorescent dye compounds which satisfy the above constraints and are excitable by laser light having a wavelength above about 630 nm.

SUMMARY

The present invention is directed towards our discovery of a class of extended rhodamine dye compounds suitable for the creation of sets of spectrally-resolvable fluorescent labels useful for multiplex fluorescent detection. The subject dye compounds are particularly well suited for use in automated fluorescence-based DNA sequencing systems using an excitation light source having a wavelength greater than about 630 nm, e.g., a helium-neon gas laser or a solid state diode laser.

In a first aspect, the invention comprises an extended rhodamine compound having the structure

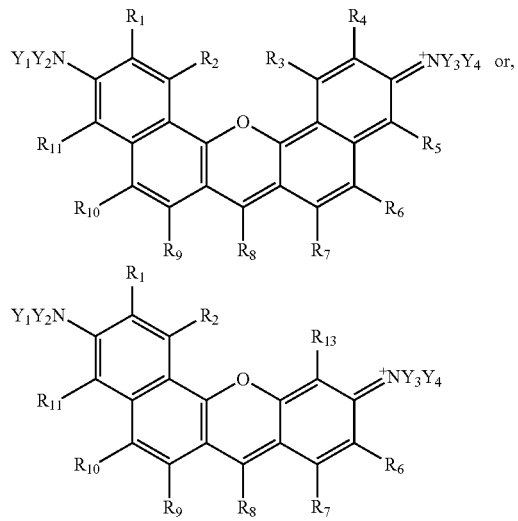

wherein the composition of moieties $R_1$ through $R_{11}$, $R_{13}$, and $Y_1$ through $Y_4$ are as follows. Taken alone, $R_1$ through $R_7$, $R_9$ through $R_{11}$, and $R_{13}$ is each independently selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —Si(O)$_2$NR, —S(O)R, —OP(O)O$_2$RR, —P(O)$_2$ RR, —C(O)OR, —NRR, —NRRR, —NC(O)R, —C(O)R, —C(O)NRR, —CN, and —OR. As used here, and throughout this Summary section, each R may be independently —H, alkyl, heteroalkyl, aryl, heteroaryl, arylalkyl, heteroarylalkyl or linking group, and each $Z_1$ may be independently any one of —R, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, —O or —OR.

$R_8$ is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$.

Taken alone, nitrogen substituents $Y_1$ through $Y_4$ are each independently selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Alternatively, rather than being taken alone, substituents $R_1$ through $R_7$, $R_9$ through $R_{11}$, $R_{13}$, $Y_1$ through $Y_4$ can be taken together in various selected combinations. In particular, $R_1$ may be taken together with $R_2$, $Y_1$ or $Y_2$, $R_2$ may be taken together with $R_1$, $R_3$ may be taken together with $R_4$, $R_4$ may be taken together with $R_3$, $Y_3$ or $Y_4$, $R_5$ may be taken together with $R_6$, $Y_3$ or $Y_4$, $R_6$ may be taken together with $R_5$, $R_7$, $Y_3$ or $Y_4$, $R_7$ may be taken together with $R_6$, $R_9$ may be taken together with $R_{10}$, $R_{10}$ may be taken together with $R_9$ or $R_{11}$, $R_{11}$ may be taken together with $R_{10}$, $Y_1$ or $Y_2$, $R_{13}$ may be taken together with $Y_1$ or $Y_2$, $Y_1$ may be taken together with $R_1$, $R_{11}$, or $Y_2$, $Y_2$ may be taken together with $R_1$, $R_{11}$, or $Y_1$, $Y_3$ may be taken together with $R_4$, $R_5$, $R_6$, $R_{13}$, or $Y_4$, or $Y_4$ may be taken together with $R_4$, $R_5$, $R_6$, $R_{13}$, or $Y_3$.

In a second aspect, the invention comprises intermediate compounds useful for the synthesis of the extended rhodamine compounds of the first aspect, such intermediates having the structure

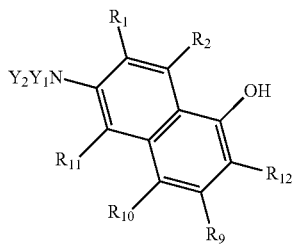

wherein the composition of moieties $R_1$, $R_2$, $R_9$ through $R_{12}$, $Y_1$ and $Y_2$ are as follows. Taken alone, $R_1$, $R_2$, $R_9$, $R_{10}$ and $R_{11}$ is each independently selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)—$_2$OR, —S(O)$_2$R, —S(O)$_3$NR, —S(O)R, —OP(O)O$_2$RR, —P(O)O$_2$RR, —C(O)OR, —NRR, —NRRR, —NC(O)R, —C(O)R, —C(O)NRR, —CN, and —OR.

$R_{12}$ is selected from the group consisting of —H and —C(O)$R_8$, wherein $R_8$ is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$.

Taken alone, nitrogen substituents $Y_1$ and $Y_2$ are each independently selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Alternatively, rather than being taken alone, moieties $R_1$, $R_2$, $R_9$, $R_{10}$, $R_{11}$, $Y_1$ and $Y_2$ can be taken together in various selected combinations. In particular, $R_1$ may be taken together with $R_2$, $Y_1$ or $Y_2$, $R_2$ may be taken together with $R_1$, $R_9$ may be taken together with $R_{10}$, $R_{10}$ may be taken together with $R_9$ or $R_{11}$, $R_{11}$ may be taken together with $R_{10}$, $Y_1$ or $Y_2$, $Y_1$ may be taken together with $R_1$, $R_{11}$, or $Y_2$, $Y_2$ may be taken together with $R_1$, $R_{11}$, or $Y_1$.

In a third aspect, the invention comprises nucleotide compounds labeled with the extended rhodamine dyes of the invention, such nucleotides having the structure

NUC-L-D

Wherein NUC is a nucleoside/tide or nucleoside/tide analog: L is a linkage; and D is an extended rhodamine dye compound of the first aspect. If NUC comprises a purine base, the linkage is attached to the 8-position of the purine, if NUC comprises a 7-deazapurine base, the linage is attached to the 7-position of the 7-deazapurine, and if NUC comprises a pyrimidine base, the linkage is attached to the 5-position of the pyrimidine.

In a fourth aspect, the invention comprises a fragment analysis method comprising the steps of forming one or more labeled polynucleotide fragments, the fragments being labeled with an extended rhodamine compound of the first aspect; resolving the one or more labeled polynucleotide fragments; and detecting the resolved labeled polynucleotide fragments.

Various aspects and/or embodiments of the above-described invention may achieve one or more of the following important advantages over known fluorescent dye compounds useful for multiplex fluorescent detection: (1) the subject dye compounds may be efficiently excited by a low-cost red laser using wavelengths at or above 630 nm; (2) the emission spectra of the subject dye compounds can be modulated by minor variations in the type and location of nitrogen and/or aryl-substituents, allowing for the creation of dye sets having similar absorption characteristics yet spectrally resolvable fluorescence emission spectra; (3) the subject dye compounds may be easily attached to nucleoside/tides or polynucleotides without compromising their favorable fluorescence properties; (4) the subject dye compounds have narrow emission bandwidths, i.e., the emission bandwidth has a full-width at half the maximum emission intensity of below about 70 nm; (5) the subject dye compounds are highly soluble in buffered aqueous solution while retaining a good quantum yield; (6) the subject dye compounds are relatively photostable; and (7) the subject dye compounds have relatively large extinction coefficients, i.e., greater than about 50,000.

These and other features and advantages of the present invention will become better understood with reference to the following detailed description and appended claims.

DETAILED DESCRIPTION OF THE PREFERRED EMBODIMENTS

Reference will now be made in detail to the preferred embodiments of the invention, example of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the scope of the invention as defined by the appended claims.

Generally, the present invention comprises a novel class of extended rhodamine dye compounds useful as fluorescent labels, methods and intermediates for synthesis of such dyes, reagents employing such dyes, and methods utilizing such dyes and reagents in the area of analytical biotechnology. The compounds of the present invention find particular application in the are of fluorescent nucleic acid analysis, e.g., automated DNA sequencing and fragment analysis, detection of probe hybridization in hybridization arrays, detection of nucleic acid amplification products, and the like.

I. Definitions

Unless stated otherwise, the following terms and phrases as used herein are intended to have the following meanings:

"Alkyl" refers to a saturated or unsaturated, branched, straight chain or cyclic monovalent hydrocarbon radical derived by the removal of one hydrogen atom from a single carbon atom of a parent alkane, alkene or alkyne. Typical alkyl groups include, but are not limited to, methyl (BCH$_3$): ethyls such as ethanyl (BCH$_2$BCH$_3$), ethenyl (BCH=CH$_2$), ethynyl (BC/CH); propyls such as propan-1-yl (BCH$_2$BCH$_2$BCH$_3$), propan-2-yl, cyclopropan-1-yl, prop-1-en-1-yl (BCH=CHBCH$_2$), prop-1-en-2-yl, prop-2-en-1-yl (BCH$_2$BCH=CH$_2$), prop-2-en-2-yl, cycloprop-1en-1-yl; cycloprop-2-en-1-yl, prop-1-yn-1-yl (BC/CBCH$_3$), prop-2-yn-1-yl (BCH$_2$CH/CH), etc.; butyls such as butan-1-yl (BCH$_2$BCH$_2$BCH$_2$BCH$_3$), butan-2-yl, cyclobutan-1-yl, but-1-en-1-yl (BCH=CH$_2$BCH$_2$BCH$_3$), but-1-en-2-yl, but-2-en-1-yl (BCH$_2$BCH=CH$_2$BCH$_3$), but-2-en-2-yl, buta-1,3-dien-1-yl (BCH=CHBCH=CH$_2$), buta-1,3-dien-2-yl, cyclobut-1-en-1-yl, cyclobut-1-en-3-yl, cyclobuta-1,3-dien-1-yl, but-1-yn-1-yl (BC/CBCH$_2$BCH$_3$), but-1-yn-3-yl, but-3-yn-1-yl (BCH$_2$BCH$_2$BC/CH), etc.; and the like. In preferred embodiments, the alkyl groups are (C$_1$-C$_6$) alkyl, with (C$_1$-C$_3$) being particularly preferred.

"Alkyleno" refers to a saturated or unsaturated, straight chain or branched acyclic hydrocarbon bridge radical derived by the removal of one hydrogen atom from each of the two terminal carbon atoms of an acyclic parent alkane, alkene or alkyne. Typical alkyleno groups include, but are not limited to, methano (BCH$_2$B); ethylenos such as ethano (BCH$_2$BCH$_2$B), etheno (BCH=CHB), ethyno (BC/CB); propylenos such as propano (BCH$_2$BCH$_2$BCH$_2$B), prop[1]eno (BCH=CHBCH$_2$B), prop[2]eno (BCH$_2$BC=CHB), prop[1]yno (BC/CBCH$_2$B), prop[1]yno (BCH$_2$BC/CB), etc.; butylenos such as butano (BCH$_2$BCH$_2$BCH$_2$BCH$_2$B), but[1]eno (BCH=CHBCH$_2$BCH$_2$B), but[2]eno (BCH$_3$BCH=CHBCH$_2$B), buta[1,3]dieno (BCH=CHBCH=CH$_2$B), but[1]yno (BC/CBCH$_2$BCH$_2$B), but[2]yno (BCBC/CH$_2$BCH$_2$B), but[1,3]diyno (BC/CBC/CB), etc.; and the like. In preferred embodiments, the alkyleno group is (C$_2$-C$_6$) alkyleno, with (C$_2$-C$_3$) being particularly preferred. Also preferred are straight chain saturated alkano radicals, e.g., ethano, propano, butano, and the like.

"Substituted alkyl" and "substituted alkyleno" refer to alkyl and alkyleno radicals, respectively, in which one or more hydrogen atoms are each independently replaced with another substituent. Typical substituents include, but are not limited to, —X, —R, —O', —OR, —SR, —S$^-$, —NRR, =NR, —CX$_3$, —CN, —OCN, —SCN, —NCO, —NCS, —NO, —NO$_2$, =N$_2$, —N$_3$, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(O)OR, —C(O))$^-$, —C(S)OR, —C(O)SR, —C(S)SR, —C(O)NRR, —C(S)NRR and —C(NR)NRR, where each X is independently a halogen and each R is independently —H, alky, aryl, arylalkyl, heteroaryl or heteroarylalkyl. Particularly preferred substituents are halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, —O and —OR, wherein R is independently selected from the group consisting of —H, alkyl, heteroalkyl, aryl, heteroaryl, arylalkyl, heteroarylalkyl and linking group.

"heteroalkyl" and "heteroalkyleno" refer to alkyl and alkyleno radicals in which one or more carbon atoms are independently replaced with the same or different heteroatoms. Typical heteroatoms to replace the carbon atom(s) include, but are not limited to, N, P, O, S, Si, etc.

"Substituted heteroalkyl" and "substituted heteroalkyleno" refer to heteroalkyl and heteroalkyleno radicals in which one or more hydrogen atoms are each independently replaced with another substituent. Typical substituents include, but are not limited to, —X, —R, —O$^-$, —OR, —SR, —S$^-$, —NRR, =NRR, —CX$_3$, —CN, —OCN, —SCN, —NCO, —NCS, —NO, —NO$_2$, =N$_2$, —N$_3$, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(O)OR, —C(O)O$^-$, —C(S)OR, —C(O)SR, —C(S)SR, —C(O)NRR, —C(S)NRR and —C(NR)NRR, where each X is independently a halogen and each R is independently —H, alkyl, aryl, arylalkyl, heteroaryl or heteroarylalkyl. Particularly preferred substituents are halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, —O and —OR, wherein R is independently selected from the group consisting of —H, alkyl, heteroalkyl, aryl, heteroaryl, arylalkyl, heteroarylalkyl and linking group.

"Aryl" refers to an unsaturated cyclic or polycyclic monovalent hydrocarbon radical having a conjugated π electron system derived by the removal of one hydrogen atom from a single carbon atom of a parent aromatic ring system. Specifically included within Aaromatic ring systems are fused ring systems in which one or more rings are aromatic and one or more rings are saturated or unsaturated, such as, for example, indane, indene, phenalene, etc. Also included within "aromatic ring systems" are non-fused ring system in which two or more identical or non-identical cyclic or polycyclic aromatic ring systems are joined directly together by a single bond, where the number of such direct ring junctions is one less than the number of aromatic ring systems involved. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, biphenyl, triphenyl, phenyl-naphthyl, binaphthyl, biphenyl-naphthyl, and the like. In preferred embodiments, the aryl group is $(C_5\text{-}C_{20})$aryl, with $(C_5\text{-}C_{10})$ being particularly preferred.

"Aryleno" refers to a divalent cyclic or polycyclic aromatic hydrocarbon bridge radical, including aryl radicals, derived by the removal of one hydrogen atom from each of two adjacent carbon atoms or a parent cyclic or polycyclic aromatic ring system. Typical aryleno groups include, but are not limited to, aceanthryleno, acenaphthyleno, acephenanthryleno, anthraceno, azuleno, benzeno, chryseno, coroneno, fluorantheno, fluoreno, hexaceno, hexapheno, hexaleno, as-indaceno, s-indaceno, indeno, naphthaleno, octaceno, octapheno, oxtaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, and the like. In preferred embodiments, the aryleno group is $(C_5\text{-}C_{20})$ aryleno, with $(C_5\text{-}C_{10})$ being particularly preferred.

"Substituted Aryl and Aryleno" refers to an aryl or aryleno radical in which one or more hydrogen atoms are each independently replaced with another substituent. Typical substituents include, but are not limited to, —X, —R, —O$^-$, —OR, —SR, —S$^-$, —NRR, =NR, —CX$_3$, —CN, —OCN, —SCN, —NCO, —NCS, —NO, —NO$_2$, =N$_2$, —N$_3$, —S(O)$_2$O$^-$, —S(O)$_2$O(H), —S(O)$_2$R, —P(O)(O$^-$)$_2$, —P(O)(OH)$_2$, —C(O)R, —C(O)X, —C(S)R, —C(O)OR, —C(O)O$^-$, —C(S)OR, —C(O)SR, —C(S)SR, —C(O)NRR, —C(S)NRR and —C(NR)NRR, where each X is independently a halogen and each R is independently —H, alkyl, aryl, arylalkyl, heteroaryl or heteroarylalkyl. Particularly preferred substituents are halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, —O and —OR, wherein R is independently selected from the group consisting of —H, alkyl, heteroalkyl, aryl, heteroaryl, arylalkyl, heteroarylalkyl and linking group.

"Heteroaryl" refers to an unsaturated cyclic or polycyclic heteroatomic radical having a conjugated π electron system derived by the removal of one hydrogen atom from a single atom of a parent heteroaromatic ring system. Specifically included within A heteroaromatic ring systems are fused ring systems in which one or more rings are aromatic and one or more rings are saturated or unsaturated, such as, for example, arsindole, chromane, chromene, indole, indoline, xanthene, etc. Typical heteroatoms include, but are not limited to, N, P, O, S, Si etc. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Heteroaryleno" refers to a cyclic or polycyclic heteroatomic bridge derived by the removal of one hydrogen atom from each of two adjacent atoms of a parent heterocyclic ring system. Typical heteroaryleno groups include, but are not limited to, acridino, carbazolo, β-carbolino, chromeno, cinnolino, furano, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, and the like. In preferred embodiments, the heteroaryleno group is a 5-20 membered heteroaryleno, with 5-10 membered heteroarylenos being particularly preferred.

"Substituted heteroaryl" and "substituted heteroaryleno" refers to a heteroaryl or heteroaryleno radical in which one or more hydrogen atoms are each independently replaced with another substituent. Typical substituents include, but are not limited to, —X, —R, —O$^-$, —OR, —SR, —S$^-$, —NRR, =NR, —CX$_2$, —CN, —OCN, —SCN, —NCO, —NCS, —NO, —NO$_2$, =N$_2$, —N$_3$, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(O)OR, —C(O)O$^-$, —C(S)OR, —C(O)SR, —C(S)SR, —C(O)NRR, —C(S)NRR and —C(NR)NRR, where each X is independently a halogen and each R is independently —H, alkyl, alkanyl, alkenyl, alkynyl, aryl, arylalkyl, heteroaryl or heteroarylalkyl, as defined herein. Particularly preferred substituents are halogen —OS(O)$_2$OR, —S(O)$_2$OR, —(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, —O and —OR, wherein R is independently selected from the group consisting of —H, alkyl, heteroalkyl, aryl, heteroaryl, arylalkyl, heteroarylalkyl and linking group.

"Arylalkyl" refers to an acyclic alkyl group in which one of the hydrogen atoms bonded to a terminal carbon atom is replaced with an aryl moiety. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is $(C_6\text{-}C_{26})$ arylalkyl, i.e., the alkanyl, alkenyl or alkynyl moiety of the arylalkyl group is $(C_1\text{-}C_6)$ and the aryl moiety is $(C_5\text{-}C_{20})$. In particularly preferred embodiments the arylalkyl group is $(C_6\text{-}C_{13})$, i.e., the alkanyl, alkenyl or alkynyl moiety of the arylalkyl group is $(C_1\text{-}C_3)$ and the aryl moiety is $(C_5\text{-}C_{10})$.

"Substituted arylalkyl" refers to an arylalkyl radical in which one or more hydrogen atoms are each independently replaced with another substituent. Typical substituents include, but are not limited to, —X, —R, —O$^-$, —OR, —SR, —S$^-$, —NRR, =NR, —CX$_3$, —CN, —OCN, —SCN, —NCO, —NCS, —NO, —NO$_2$, =N$_2$, —N$_3$, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(O)OR, —C(O)O$^-$, —C(S)OR, —C(O)SR, —C(S)SR, —C(O)NRR, —C(S)NRR and —C(NR)NRR, where each X is independently a halogen and each R is independently —H, alkyl, alkanyl, alkenyl, alkynyl, aryl, arylalkyl, heteroaryl or heteroarylalkyl, as defined herein. Particularly preferred substituents are halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, —O and —OR, wherein R is independently selected from the group consisting of —H, alkyl, heteroalkyl, aryl, heteroaryl, arylalkyl, heteroarylalkyl and linking group.

"Heteroarylalkyl" refers to an acyclic alkyl group in which one of the hydrogen atoms bonded to a terminal carbon atom is replaced with a heteroaryl moiety. Where specific alkyl moieties are intended, the nomenclature heteroarylalkanyl, heteroarylakenyl and/or a heteroarylalkynyl is used. In preferred embodiments, the heteroarylalkyl group is a 6-26 membered heteroarylalkyl, i.e., the alkanyl, alkenyl or alkynyl moiety of the heteroarylalkyl is ($C_1$-$C_6$) and the heteroaryl moiety is a 5-20 membered heteroaryl. In particularly preferred embodiments, the heteroarylalkyl is a 6-13 membered heteroarylalkyl, i.e., the alkanyl, alkenyl or alkynyl moiety is ($C_1$-$C_3$) and the heteroaryl moiety is a 5-10 membered heteroaryl.

"Substituted heteroarylalkyl" refers to a heteroarylalkyl radical in which one or more hydrogens are each independently replaced with another substituent. Typical substituents include, but are not limited to —X, —R, —$O^-$, —OR, —SR, —$S^-$, —NRR, =NR, —$CX_3$, —CN, —OCN, —SCN, —NCO, —NCS, —NO, —$NO_2$, =$N_2$, —$N_3$, —$S(O)_2O^-$, —$S(O)_2OH$, —$S(O)_2R$, —$P(O)(O^-)_2$, —$P(O)(OH)_2$, —C(O)R, —C(O)X, —C(S)R, —C(O)OR, —$C(O)O^-$, —C(S)OR, —C(O)SR, —C(S)SR, —C(O)NRR, —C(S)NRR and —C(NR)NRR, where each X is independently a halogen and each R is independently —H, alkyl, alkanyl, alkenyl, alkynyl, aryl, arylalkyl, heteroaryl or heteroarylalkyl, as defined herein. Particularly preferred substituents are halogen, —$OS(O)_2OR$, —$S(O)_2OR$, —$S(O)_2R$, —$S(O)_2NR$, —S(O)R, —$OP(O)O_2RR$, —$P(O)O_2RR$, —C(O)OR, —NRR, —NRRR, —NC(O)R, —C(O)R, —C(O)NRR, —CN, —O and —OR, wherein R is independently selected from the group consisting of —H, alkyl, heteroalkyl, aryl, heteroaryl, arylalkyl, heteroarylalkyl and linking group.

"Spectral resolution" in reference to a set of dyes means that fluorescent emission bands of the dyes are sufficiently distinct, i.e., sufficiently non-overlapping, that reagents to which the set of dyes are attached, e.g. polynucleotides, can be distinguised on the basis of the fluorescent emission bands generated by each of the individual members of the set of dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811, 218, or in Wheeless et al. pgs. 21-76, in *Flow Cytometry: Instrumentation and Data Analysis* (Academic Press, New York, 1985).

"Linking group" means a moiety capable of reacting with a "complementary functionality" to form a "linkage." A linking group and its associated complementary functionality are referred to herein as a "linkage pair."

The term "nucleoside" refers to a compound comprising a purine, deazapurine, or pyrimidine nucleobase, e.g., adenine, guanine, cytosine, uracil, thymine, 7-deazaadenine, 7-deazaguanesine, and the like, that is linked to a pentose at the 1'-position. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine, (e.g., Kornberg and Baker, *DNA Replication*, 2nd Ed. (Freeman, San Francisco, 1992)). The term "nucleotide" as used herein refers to a phosphate ester of a nucleoside, e.g., a triphosphate ester, wherein the most common size of esterification is the hydroxyl group attached to the C-5 position of the pentose. The term "nucleoside/tide" as used herein refers to a set of compounds including both nucleosides and nucleotides.

The term "polynucleotide" means polymers of nucleotide monomers, including analogs of such polymers, including double and single stranded deoxyribonucleotides, ribonucleotides, α-anomeric forms thereof, and the like. Monomers are linked by "internucleotide linkages," e.g. phosphodiester linkages, where as used herein, the term "phosphodiester linkage" refers to phosphodiester bonds or bonds including phosphate analogs thereof, including associated counterions, e.g., $H^+$, $NH_4^+$, $Na^+$, if such counterions are present. Whenever a polynucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes deoxythymidine, unless otherwise noted.

"Analogs" in reference to nucleoside/tides and/or polynucleotide comprise synthetic analogs having modified nucleobase portions, modified pentose portions and/or modified phosphate portions, and, in the case of polynucleotides, modified internucleotide linkages, as described generally elsewhere (e.g., Scheit, *Nucleotide Analogs* (John Wiley, New York, 1980); English, *Angew. Chem. Int. Ed. Engl.* 30-613-29 (1991); Agrawal, *Protocols for Polynucleotides and Analogs*, Humana Press (1994). Generally, modified phosphate portions comprise analogs of phosphate wherein the phosphorous atom is in the +5-oxidation state and one or more of the oxygen atoms is replaced with a non-oxygen moiety, e.g., sulfur, Exemplary phosphate analogs include but are not limited to phosphorothioate, phosphorocithioate, phosphoroselenoate, phosphorodiselenoate, phosphoroanilothioate, phosphoranilidate, phosphoramidate, boronophosphates, including associated counterions, e.g., $H^+$, $NH_2^+$, $Na^+$, if such counterions are present. Exemplary modified nucleobase portions include but are not limited to 2,6-diaminopurine, hypoxanthine, pseudouridine, C-5-propyne, isocytosine, isoguanine, 2-thiopyrimidine, and other like analogs. Particularly preferred nucleobase analogs are iso-C and iso-G nucleobase analogs available from Sulfonics, Inc., Alachua, Fla. (e.g., Benner, et al., U.S. Pat. No. 5,432,272). Exemplary modified pentose portions include but are not limited to 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, bromo and the like. Modified internucleotide linkages include phosphate analogs, analogs having achiral and uncharged intersubunit linkages (e.g., Sterchak, E. P., et al., *Organic Chem*, 52:4202 (1987)), and uncharged morpholino-based polymers having achiral intersubunit linkages (e.g., U.S. Pat. No. 5,034,506). A particularly preferred class of polynucleotide analogs where a conventional sugar and internucleotide linkage has been replaced with a 2-aminoethylglycine amide backbone polymer nucleic acid (PNA) (e.g., Nielsen et al., *Science*, 254-1497-1500 (1991); Egholm et al., *J. Am. chem. Soc.*, 114: 1895-1897 (1992)).

As used herein the term "primer-extension reagent" means a reagent comprising components necessary to effect an enzymatic template-mediated extension of a polynucleotide primer. Primer extension reagents include (1) a polymerase enzyme, e.g., a thermostable DNA polymerase enzyme such as Taq polymerase; (2) a buffer; (3) one or more chain-extension nucleotides, e.g., deoxynucleotide triphosphates, e.g., deoxyguanosine 5'-triphosphate, 7-deazadeoxyguanosine 5'-triphosphate, deoxyadenosine 5'-triphosphate, deoxythymidine 5'-triphosphate, deoxycytidine 5'-triphosphate; and, optionally in the case of Sanger-type DNA sequencing reactions, (4) one or more chain-terminating nucleotides, e.g., dideoxynucleotide triphosphates, e.g., dideoxyguanosine 5'-triphosphate, 7-deazadideoxyguanosine 5'-triphosphate, dideoxyadenosine 5'-triphosphate, dideoxythymidine 5'-triphosphate, and dideoxycytidine 5'-triphosphate.

"Terminator" means a chemical entity that when incorporated into 3'-end of a primer extension product prevents the further extension of such primer extension product. In the case of nucleotide terminators, when the nucleotide terminator includes a ribofuranose sugar portion, the 3'-position must not have a hydroxy group capable of being subsequently used by a polymerase to incorporate additional nucleotides. Alternatively, a ribofuranose analog could be used, such as arabinose. Exemplary nucleotide terminators include 2',3'-dideoxy-β-D-ribofuranosyl, β-D-arabinofuranosyl, 3'-deoxy-β-D-arabinofuramoyl, 3'-amino-2',3'-dideoxy-β-D-ribofuranosyl, and 2',3'-dideoxy-3'-fluoro-β-D-ribofuranosyl (Chidgeavadze et al., *Nucleic Acids Research*, 12: 1671-1686 (1984); and Chidgeavadze et al., *FEB Lett.*, 183: 275-278 (1985)). Nucleotide terminators also include reversable nucleotide terminators (Metzker et al., *Nucleic Acids Research*, 22(20); 4259 (1994)).

"Water solubilizing group" means a substituent which increases the solubility of the compounds of the invention in aqueous solution. Exemplary water-solubilizing groups include but are not limited charged or polar groups, e.g., quaternary amine, sulfate, sulfonate, carboxylate, phosphate, polyether, polyhydroxyl, and boronate.

Those of skill in the art will appreciate that many of the compounds encompassed by the formulae referred to herein contain chiral centers. In addition, the carious compounds may further exhibit the phenomena of tautomerism, conformational isomerism, or geometric isomerism. As the formulae drawings within this specification can represent only one of the possible tantomeric, conformational isomeric, enantiomeric or geometric isomeric forms, it should be understood that the invention encompasses any tautomeric, conformational isomeric, enantiomeric or geometric isomeric forms of the compounds which exhibit the desired activities and/or properties described herein. In addition, all molecular structure referred to herein, either through diagrams or terminology, are intended to encompass all protonation states and associated counterions thereof.

II. Extended Rhodamine Dye Compounds

In a first aspect, the present invention comprises a moved class of extended rhodamine compounds having the general structure shown in Formula I immediately below.

FORMULA I

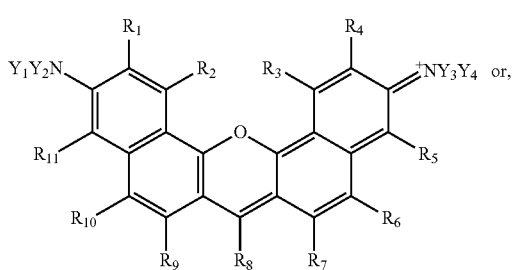

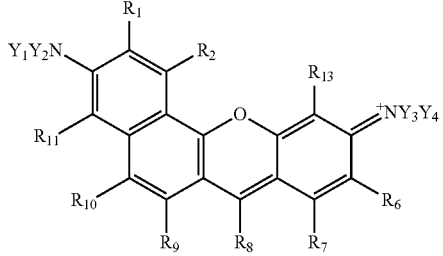

The moiety $R_1$ in the structures of Formula I taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

As used here and throughout this disclosure, the substituent $Z_1$ is selected from the group consisting of —R, halogen, —OS(O)$_2$OR, —S(O)$_2$OR, —S(O)$_2$R, —S(O)$_2$NR, —S(O)R, —OP(O)$_2$RR, —P(O)O$_2$RR, —C(O)OR, —NRR, —NRRR, —NC(O)R, —C(O)R, —C(O)NRR, —CN, —O and —OR, wherein R is independently selected from the group consisting of —H, alkyl, heteroalkyl, aryl, heteroaryl, arylalkyl, heteroarylalkyl and linking group.

Alternatively, $R_1$ may be taken together with $R_2$, $Y_1$, or $Y_2$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_2$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Alternatively, $R_2$ may be taken together with $R_1$, where the combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_3$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Or, $R_3$ may be taken together with $R_4$, where the combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_4$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

$R_4$ may be taken together with $R_3$, $Y_3$, or $Y_4$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

Moiety $R_5$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Alternatively, $R_5$ may be taken together with $R_6$, $Y_3$, or $Y_4$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_6$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Or, $R_6$ may be taken together with $R_5$, $R_7$, $Y_3$, or $Y_4$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The substituent $R_2$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Or, $R_7$ may be taken together with $R_6$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_8$ is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$.

In one preferred embodiment $R_8$ is alkyl independently substituted with one or more substituents selected from the group consisting of halogen, —C(O)R, and —S(O)$_2$R wherein R is independently selected from the group consisting of —H, alkyl, heteroalkyl, aryl, heteroaryl, arylalkyl, heteroarylalkyl and linking group. In a particularly preferred embodiment, R is selected from the group consisting of —OH, —O-alkyl, —NH$_2$, —N-alkyl and linking group.

In another preferred embodiment $R_8$ is —CF$_3$.

In yet another preferred embodiment, $R_8$ is

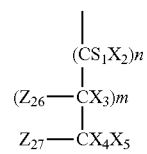

wherein $Z_{26}$ and $Z_{27}$ are each independently selected from the group consisting of hydrogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —NC(O)R, R, and —OR, wherein R is independently selected from the group consisting of —H, alkyl, heteroalkyl, aryl, heteroaryl, arylalkyl, heteroarylalkyl and linking group. And, $X_1$, $X_2$, $X_3$, and $X_5$ are each independently selected from the group consisting of hydrogen, —Cl, —Br and —F. Indicies n and m are integers each independently ranging from 0 to 5. In two particularly preferred embodiments, $X_1$ and $X_2$ are each —H, or alternatively, $X_1$, $X_2$, $X_4$, and $X_5$ are each —F.

In a particularly important preferred embodiment of the compounds of the present invention, $R_8$ has the structure

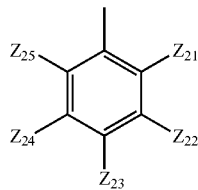

wherein $Z_{21}$, $Z_{22}$, $Z_{23}$, $Z_{24}$ and $Z_{25}$ are taken separately are $Z_1$. In one particularly preferred embodiments, $Z_{21}$, $Z_{22}$, $Z_{23}$, $Z_{24}$ and $Z_{25}$ are each independently selected from the group consisting of —H, halogen, $C_1$ to $C_3$ alkyl, —C(O)OR, —C(O)R, —S(O)$_2$OR, —S(O)$_2$R, and —CH$_2$OR, wherein R is independently selected from the group consisting of —H, alkyl, heteroalkyl, aryl, heteroaryl, arylalkyl, heteroarylalkyl and linking group. In another particularly preferred embodiment, one or more of $Z_{21}$, $Z_{22}$, $Z_{23}$, $Z_{24}$ or $Z_{25}$ is —F or —Cl. In yet another particularly preferred embodiment, $Z_{21}$ is —C(O)OH. In another particularly preferred embodiment, $Z_{21}$ is —C(O)OH, and one of $Z_{23}$ or $Z_{24}$ is —C(O)OH. In yet another particularly preferred embodiment $Z_{22}$ and $Z_{23}$ are each —Cl. In another particularly preferred embodiment $Z_{22}$, $Z_{23}$, $Z_{24}$ and $Z_{25}$ are all —F or all Cl. In another particularly preferred embodiment, $Z_{21}$ is —S(O)$_2$OH and one of $Z_{23}$ or $Z_{24}$ is —C(O)OH. In yet another particularly preferred embodiment, $Z_{21}$ is —C(O)OR and one of $Z_{22}$, $Z_{23}$, or $Z_{24}$ is linking group.

In another preferred embodiment, $R_8$ is selected from among the group consisting of

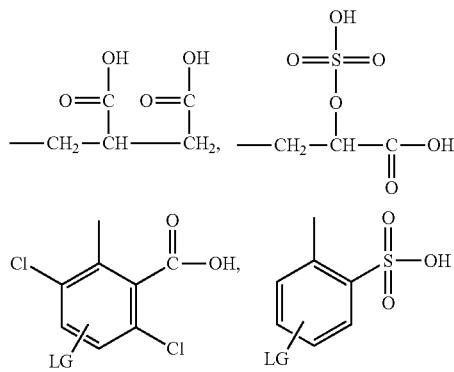

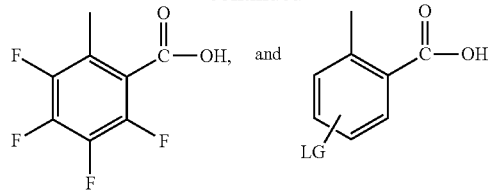

wherein LG is linking group.

The moiety $R_9$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Alternatively, $R_9$ may be taken together with $R_{10}$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

$R_{10}$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_3$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Or, when $R_{10}$ is taken together with $R_9$ or $R_{11}$, the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

$R_{11}$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Alternatively, $R_{11}$ may be taken together with $R_{10}$, $Y_1$ or $Y_2$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

$R_{13}$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Alternatively, $R_{13}$ may be taken together with $Y_3$ or $Y_4$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

In one preferred embodiment, one or more of $R_1$, $R_4$, $R_5$, $R_6$, $R_7$, $R_9$, $R_{10}$, $R_{11}$ and $R_{13}$ is each independently —S(O)$_2$OH, or is each independently —F or —Cl, or is each independently aryl or aryl independently substituted with one or more $Z_1$.

$Y_1$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Or, $Y_1$ may be taken together with $R_1$, $R_{11}$ or $Y_2$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

Moiety $Y_2$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Alternatively, $Y_2$ may be taken together with $R_1$, $R_{11}$ or $Y_1$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituent with one or more $Z_1$, heteroaryleno, and heteroaryleno independently substituted with one or more $Z_1$.

$Y_3$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Or, $Y_3$ may be taken together with $R_4$, $R_5$, $R_6$, $R_{13}$ or $Y_4$, where the resulting combined substituent is selected from the group consisting of alkyleno, alkyleno independently substituent with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

$Y_4$ is absent, or $Y_4$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Instead, $Y_4$ may be taken together with $R_4$, $R_5$, $R_6$, $R_{13}$ or $Y_3$, where the resulting combined substituent is selected from the group consisting of alkyleno, alkyleno independently substituent with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

In one preferred embodiment, at least one of $Y_1$, $Y_2$, $Y_3$, or $Y_4$ taken separately is selected from the group consisting of —H, alkyl, aryl and arylalkyl.

In another preferred embodiment of the compounds of the present invention, $Y_1$ is taken together with $R_1$ or $R_{13}$ and is $C_2$ or $C_3$ alkyleno or alkyleno independently substituted with one or more $Z_1$, or $Y_2$ is taken together with $R_1$ or $R_{11}$ and is $C_2$ or $C_3$ alkyleno or alkyleno independently substituted with one or more $Z_1$, or $Y_3$ is taken together with $R_4$ or $R_5$ or $R_6$ or $R_{13}$ and is $C_2$ or $C_3$ alkyleno or alkyleno independently substituted with one or more $Z_1$, or $Y_4$ is taken together with $R_4$ or $R_5$ or $R_6$ or $R_{13}$ and is $C_2$ or $C_3$ alkyleno or alkyleno independently substituted with one or more $Z_1$. In a particularly preferred embodiment, the $C_2$ or $C_3$ substituted alkyleno is gem disubstituted with $C_1$ to $C_3$ alkyl, most preferably methyl.

Several exemplary preferred structures are provided immediately below.

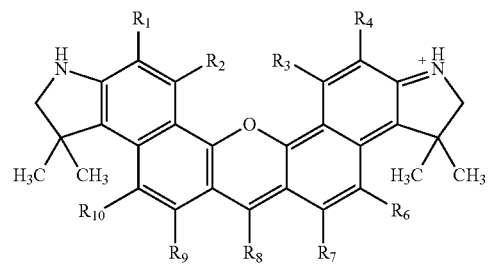

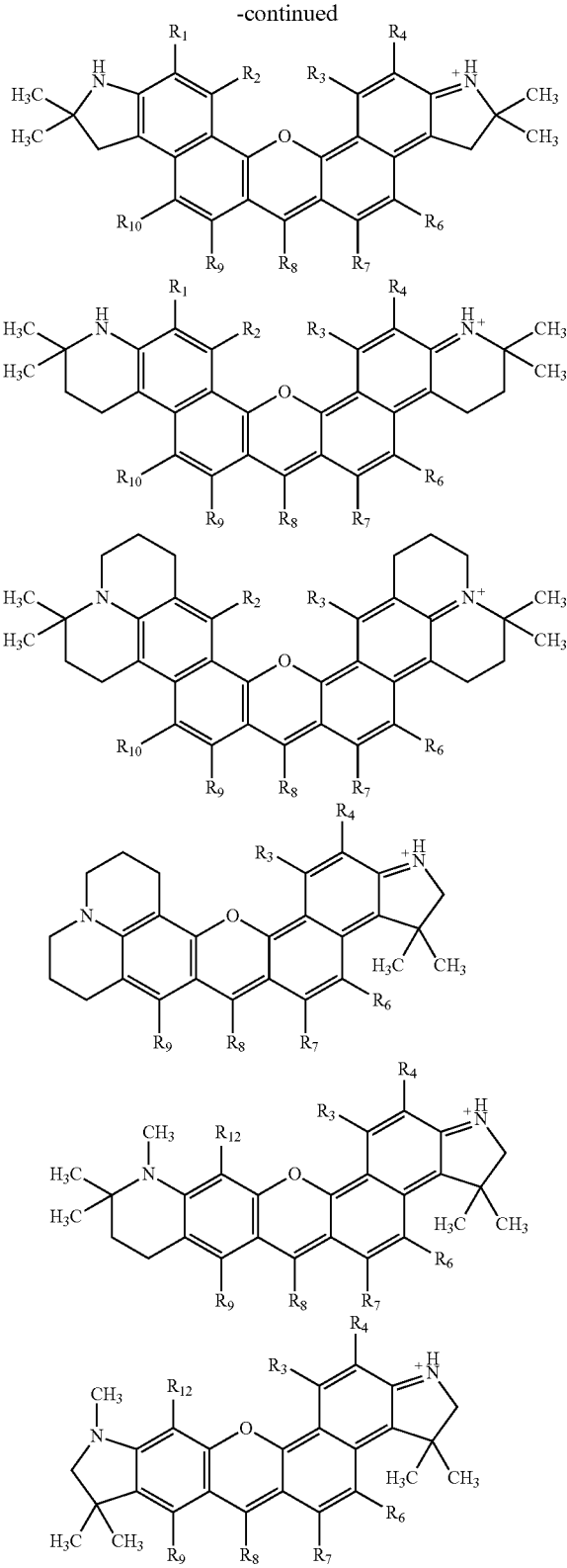

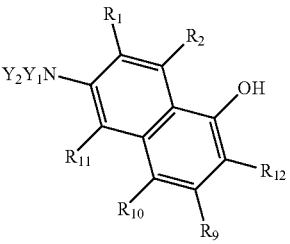

FORMULA II

The moiety $R_1$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)$_2$RR, —C(O))R, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Alternatively, when $R_1$ is taken together with $R_2$, $Y_1$, and $Y_2$, the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_2$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Or, $R_2$ may be taken together with $R_1$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_9$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Alternatively, $R_9$ may be taken together with $R_{10}$, where the resulting combined substituent is selected from the group

III. Amino Hydroxy Napthyl Intermediate Compounds

In a second aspect, the present invention comprises a novel class of amino hydroxy napthyl intermediate compounds useful for the preparation of the above-described extended rhodamine compounds, the general structure of which is provided immediately below.

consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_{10}$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR wherein R is independently selected from the group consisting of —H, alkyl, heteroalkyl, aryl, heteroaryl, arylalkyl, heteroarylalkyl and linking group.

Or, $R_{10}$ may taken together with $R_9$ or $R_{11}$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $R_{11}$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NRR, —NRRR, —NC(O)R, —C(O)R, —C(O)NRR, —CN, and —OR, wherein R is independently selected from the group consisting of —H, alkyl, heteroalkyl, aryl, heteroaryl, arylalkyl, heteroarylalkyl and linking group.

Alternatively, $R_{11}$ may be taken together with $R_{10}$, $Y_1$ or $Y_2$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

In a preferred embodiment, one or more of $R_1$, $R_2$, $R_9$, $R_{10}$ and $R_{11}$ is each independently —S(O)$_2$OH. In another preferred embodiment, one or more of $R_1$, $R_2$, $R_9$, $R_{10}$ and $R_{11}$ is each independently —F or —Cl. In yet another preferred embodiment, one or more of $R_1$, $R_2$, $R_9$, and $R_{10}$ and $R_{11}$ is each independently aryl or aryl independently substituted with one or more $Z_1$.

The moiety $R_{12}$ is selected from the group consisting of —H and —C(O)$R_8$, where $R_8$ is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$.

The moiety $Y_1$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Alternatively, $Y_1$ may be taken together with $R_1$, $R_{11}$ or $Y_2$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The moiety $Y_2$ taken alone is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Alternatively, $Y_2$ may be taken together with $R_1$, $R_{13}$ or $Y_1$, where the resulting combined substituent is selected from the group consisting of alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

In one preferred embodiment, at least one of $Y_1$ or $Y_2$ taken separately is selected from the group consisting of —H, alkyl, aryl and arylalkyl.

In another preferred embodiment, $Y_1$ is taken together with $R_1$ or $R_{11}$ and is $C_2$ or $C_3$ alkyleno or alkyleno independently substituted with one or more $Z_1$, or $Y_2$ is taken together with $R_1$ or $R_{11}$ and is $C_2$ or $C_3$ alkyleno or alkyleno independently substituted with one or more $Z_1$. Preferably, the $C_2$ or $C_3$ substituted alkyleno is gem disubstituted with $C_1$ to $C_3$ alkyl, most preferably methyl.

Several exemplary preferred structures according to this embodiment are provided immediately below

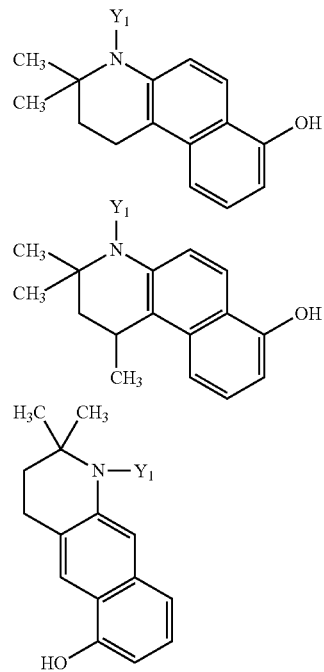

-continued

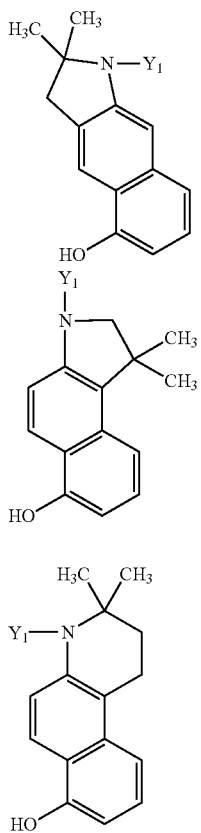

IV. Synthesis of Extended Rhodamine Dye Compounds and Amino Hydroxy Napthyl Intermediates A. Synthesis of Extended Rhodamine Dyes. Several synthetic methods are available for the synthesis of the extended rhodamine dyes of the present invention.

A first preferred synthesis method is summarized below in Scheme 1. This first method yields a symmetrically substituted extended rhodamine dye, i.e., a dye in which moieties $R_1$ and $R_4$ are the same, moieties $R_2$ and $R_3$ are the same, moieties $R_{11}$ and $R_5$ are the same, moieties $R_{10}$ and $R_6$ are the same, moieties $R_9$ and $R_7$ are the same, moieties $Y_1$ and $Y_3$ are the same, and moieties $Y_2$ and $Y_4$ are the same. In the first preferred method, one equivalent of an aminonaphthol intermediate 1 and one equivalent of an aminonaphthol intermediate 2, where moieties $R_1$, $R_2$, $R_{11}$, $R_{10}$, $R_9$, $Y_1$ and $Y_2$ of intermediate 1 are the same as moieties $R_4$, $R_3$, $R_5$, $R_6$, $R_7$, $Y_3$ and $Y_4$ of intermediate 2, respectively, are combined with one equivalent of carboxylic acid intermediate 3 in the presence of a strong acid, e.g., sulfuric acid, methane sulfonic acid, or triflic acid, or alternatively a Lewis acid such as aluminum chloride or zinc chloride. At least 3 molar equivalents of acid, based on molar equivalents of intermediate 3, are used. The reaction is conducted in an inert solvent, e.g., methylene chloride or nitrobenzene, or no solvent other than the acid. The reaction is heated at temperatures from about 50° C. to about 200° C. from about 1 hr to about 24 hr under an inert atmosphere of nitrogen, helium, argon, or other non-reactive gas. The condensation yields the extended rhodamine dye 4 in a single step. The acid is removed by dissolution of the reaction mixture into a water insoluble solvent, such as methylene dichloride, and extraction of the acid with water. The product can be isolated from the by-products and starting materials by chromatography on silica gel, with for example, a ternary solvent system such as methylene dichloride:methanol:acetic acid in ratios of about 200:20:5 to about 20:20:5, respectively.

Scheme 1

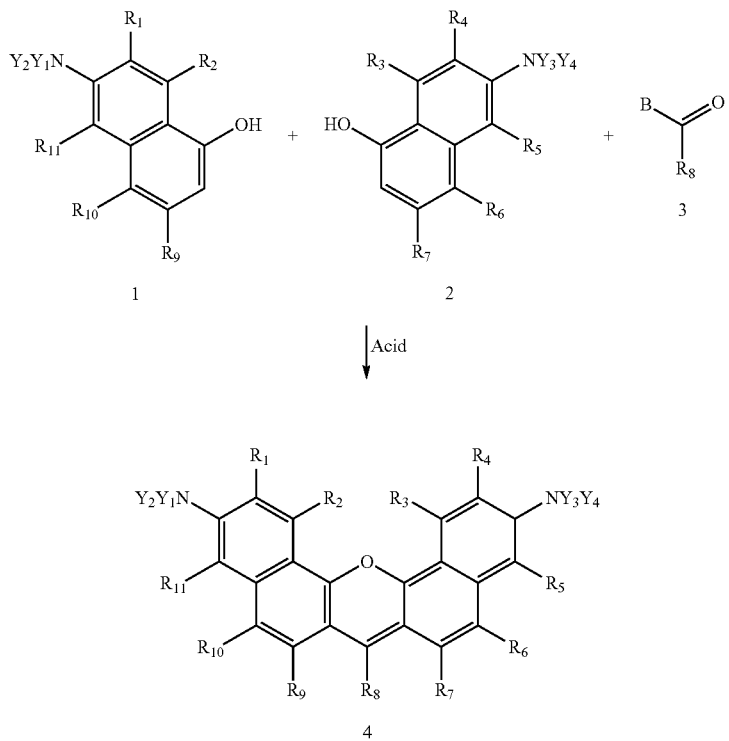

A second preferred synthesis method is summarized below in Schemes 2a and 2b. This second method can yield either a symmetrically substituted or non-symmetrically substituted extended rhodamine dye. In this second preferred method, one equivalent of an aminonaphthol intermediate 1 is reacted with one equivalent of an activated form of the carboxylic acid intermediate 3, e.g. in the form of the acid chloride derivative of intermediate 3, in the presence of a Lewis acid catalyst, e.g., aluminum chloride, in a solvent, e.g., nitrobenzene, to yield an aminonaphthol ketone intermediate 5. The ketone 5 is isolated by dissolution of the reaction mixture into a water insoluble solvent, such as methylene dichloride, and extraction aluminum salts with aqueous acid such as HCl. The ketone product can be isolated from impurities and starting materials by chromatography on silica gel, with, for example, a ternary solvent system such as methylene dichloride:methanol:acetic acid in ratios of about 200:20:5 to about 20:20:5, respectively, The purified ketone 5 is then reacted with one equivalent of a second aminonaphthol intermediate 2 in the presence of a strong acid, such a sulfuric acid, methane sulfonic acid, or triflic acid, or a Lewis acid such as aluminum chloride or zinc chloride. At least 3 molar equivalents of acid, based on molar equivalents of intermediate 2, are used with an inert solvent such as methylene chloride or nitrobenzene, or no solvent other than the acid catalyst. The reaction is heated at about 50° C. to about 200° C. from about 1 hr to about 24 hr under an inert atmosphere, e.g., nitrogen, helium, argon, or other non-reactive gas. The acid is then removed by dissolution of the reaction mixture into a water insoluble solvent, such as methylene dichloride, and extraction of the acid with water. The product can be isolated from the by-products and starting materials by chromatography on silica gel, with, for example, a ternary solvent system such as methylene dichloride:methanol:acetic acid in ratios of about 200:20:5 to about 20:20:5, respectively. (Scheme 2a). Alternatively, the ketone 5 is reacted with one equivalent of a meta-hydroxy aniline 70 under the same reaction conditions and isolation procedures described for Scheme 2a to yield the hybrid rhodamine-extended rhodamine dye 71 shown in Scheme 2b.

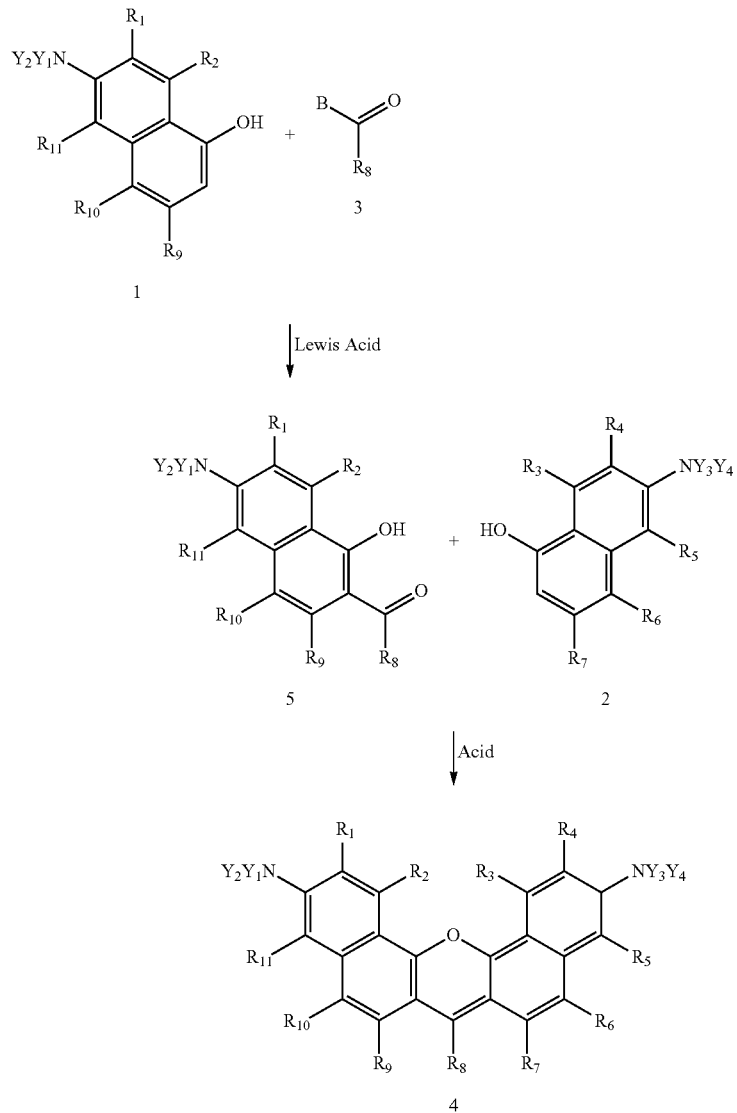

Scheme 2a

Scheme 2b

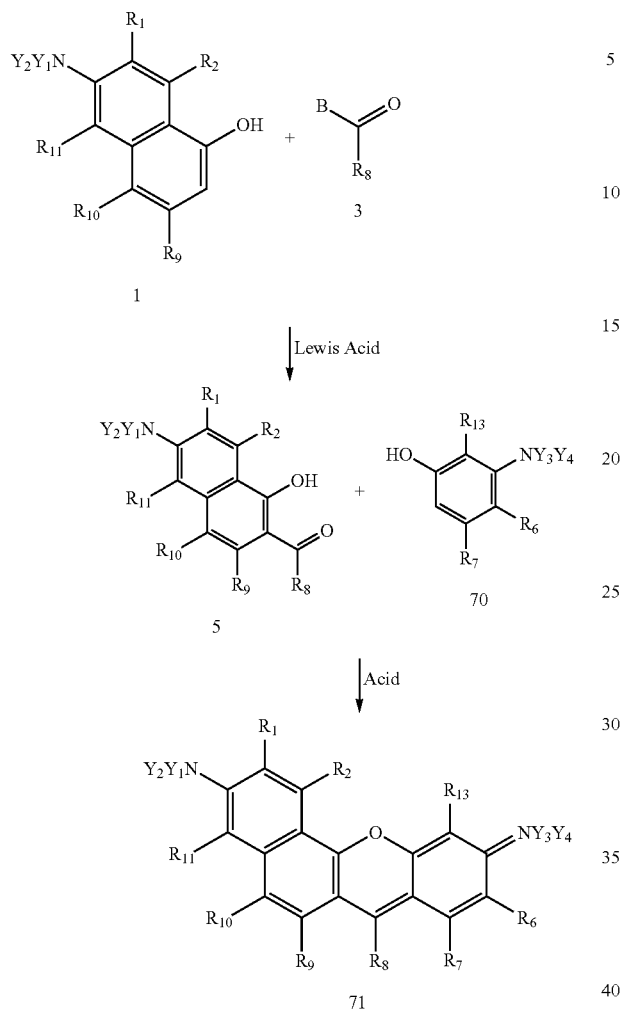

Scheme 3

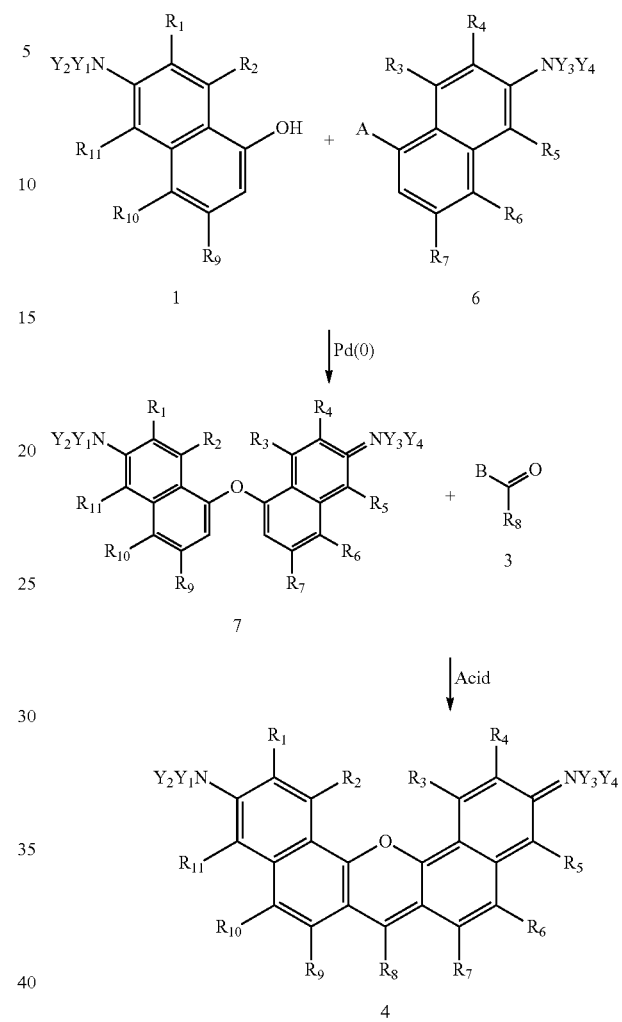

A third synthetic method which can yield either a symmetrical or unsymmetrical dye 4 is summarized below in Scheme 3. In this method, when none of $Y_1$, $Y_2$, $Y_3$ and $Y_4$ hydrogen, a diaryl ether 7 is synthesized by a condensation of intermediate 1 with intermediate 6, where A is bromine, iodine, triflate, or other group that is active toward catalysis with transition metals. For example, when A is bromide or iodide, intermediate 1 and intermediate 6 are condensed under conditions of the Ullmann Reaction with sodium hydroxide at temperatures or 150° C. to 200° C. in inert solvents such as N-methylpyrrolidone in the presence of Cu(I) salts. Alternatively, the condensation is performed with the same intermediates using cesium carbonate at 80° C. to 100° C. in toluene in the presence of palladium. However, if $Y_1$ or $Y_2$ on 7 is hydrogen, or if $Y_3$ or $Y_4$ on 6 is hydrogen, prior to the condensation reaction, the associated nitrogen must be protected. An example of a nitrogen protecting group that is stable to the basic conditions used for the transition metal catalysts is t-butyl carbamate, which is prepared from chloro-t-butylcarbonate and the aminonaphthol intermediate 1 and/or the naphthylamine intermediate 6. The protecting group is then removed from compound 7 using a strong acid such as trifluoroacetic acid. Following the condensation reaction, the ether 7 is then reacted with properly substituted intermediate 3 in the presence of acid and heat to yield the dye 4.

B. Synthesis of Intermediate Compounds.

Compound 3. Two preferred generalized structures (8 and 9) of compound 3 are presented immediately below. Substituent B on 8 or 9 may be —OH, a halogen, e.g., —F, —Cl, —Br, —OS(O)$_2$OH, or —C(O)OH. Alternatively, when B is taken together with $Z_{25}$ of compound 8 or $Z_{26}$ of compound 9, the combination is preferably —C(O)O—, or —S(O)O—, or any other group useful for activation of a carboxylic acid. Preferred X, $Z_{21}$, $Z_{22}$, $Z_{23}$, $Z_{24}$, $Z_{25}$, $Z_{26}$, and $Z_{27}$ are as discussed above.

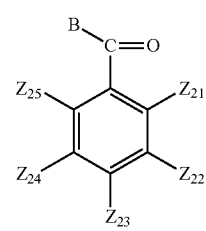

-continued

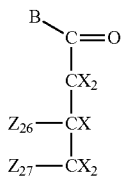
9

Compound 19. Compound 19 may be prepared in 12 steps from substituted naphthalene 10 as shown below in Scheme 5. Compound 10 is converted to its triflate 11 by reaction with trifluoromethane sulfonyl chloride in pyridine. Next, compound 11 is reacted with 2-sodium dimethyl malonate in the presence of a palladium catalyst to yield malonate derivative 12. The methyl esters of 12 are hydrolyzed to di-carboxylates with sodium hydroxide in methanol, and the di-acid is obtained after neutralization with a strong acid such as HCl. The diacid is decarboxylated at elevated temperature to yield acetic acid derivative 13. The carboxylic acid 13 is converted to its acid chloride with oxalyl chloride in an inert solvent such as methylene dichloride; the acid chloride is isolated by removal of the solvent and the excess oxalyl chloride by evaporation, and is converted to the amide 14 by reaction with an amine in an inert solvent such as methylene dichloride. The methyl group on 14 is removed with HBr to yield the phenol 15, and 15 is then converted to triflate 16 with trifluoromethane sulfonyl chloride in pyridine. The amide hydrogen is removed by reaction with sodium hydride, followed by displacement of the triflate with the amide anion catalyzed with palladium in a solvent such as toluene to yield the lactam 17. The amide carbonyl portion of 17 is removed by reduction with lithium aluminum hydride in an ether solvent such as diethyl ether yielding cyclic amine 18. The nitro group on 18 is reduced to a primary amino group by reduction with palladium catalyst and hydrogen gas in a solvent that is inert to hydrogenation such as methanol; the primary amino group is converted to its diazonium salt with nitrous acid in water, and the diazo group is displaced with hydroxide by treatment with aqueous sodium hydroxide to yield the aminonaphthol dye intermediate 19. The intermediate 19 is isolated by neutralization of the reaction mixture with a strong acid, such as HCl, and extraction of 19 from the aqueous mixture into an organic solvent, such as methylene dichloride.

Compound 23. Nitro lactam 17 in Scheme 5 is converted to its imidate ester 20 by reaction with trimethyloxonium tetrafluoroborate in methylene chloride. The methoxy group of the imidate ester is then displaced with a methyl group using methyl lithium in toluene to yields the gem-dimethyl cyclic amine 21. The nitro group on 21 is reduced to an amino group by reduction with palladium and hydrogen gas in a solvent that is inert to hydrogenation such as methanol; the amino group is then converted to its diazonium salt with nitrous acid in water to yield 22, and the diazo group is displaced with hydroxide by treatment with aqueous sodium hydroxide to yield the aminonaphthol dye intermediate 23. The intermediate 23 is isolated by neutralization of the reaction mixture with a strong acid, such as HCl, and extraction of 23 from the aqueous mixture into an organic solvent, such as methylene dichloride. Note that the substituent R in Scheme 5 is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl; heteroaryl independently substituted with one or more $Z_1$, arylalkyl, arylalkyl independently substituted with one or more $Z_1$, heteroarylalkyl, and heteroarylalkyl independently substituted with one or more $Z_1$.

Scheme 5

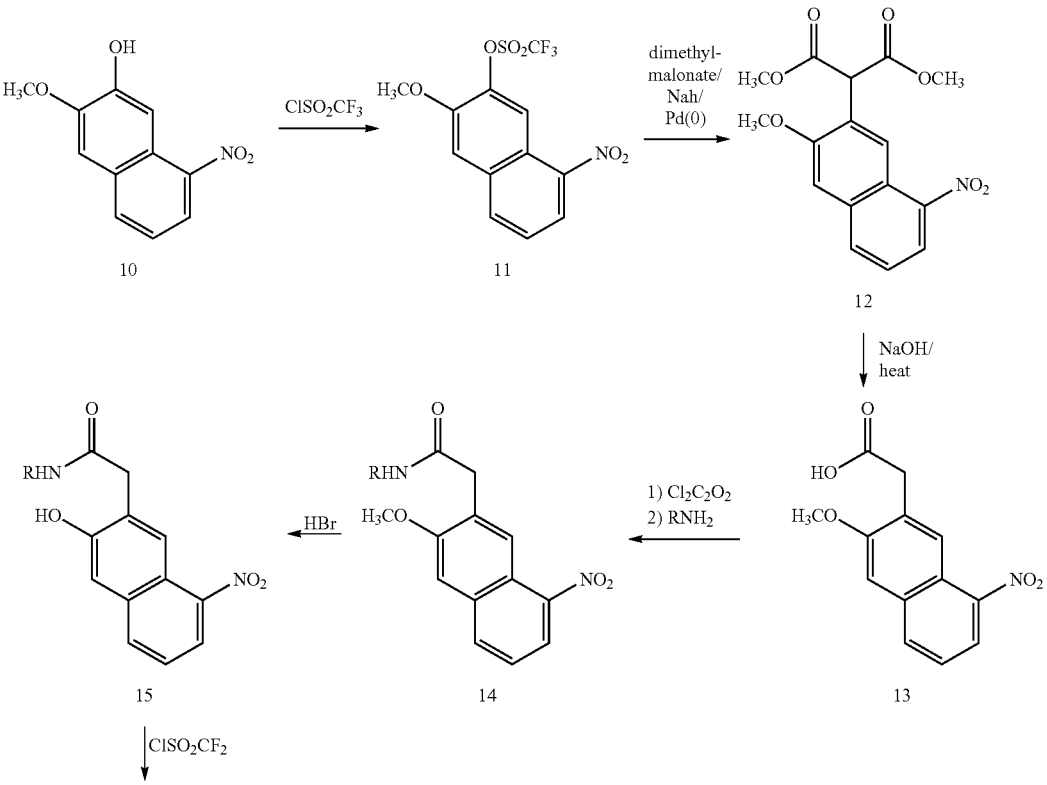

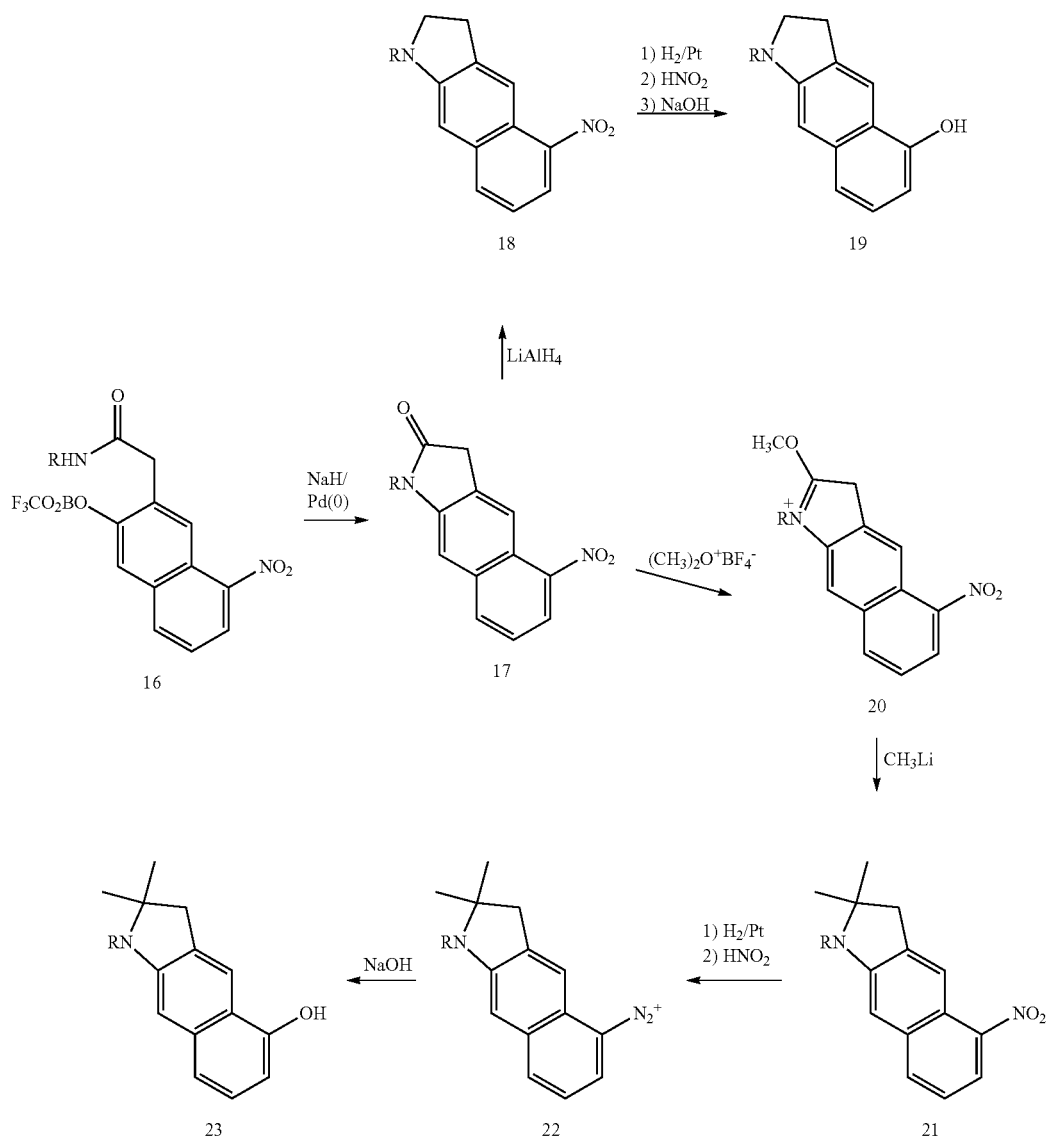

Compound 27. Compound 27 may be prepared in 3 steps from aminophenol 24 as shown in Scheme 6 below. Aminonaphthol 24 is acylated on the nitrogen with 2-bromoacetyl chloride in pyridine, yielding amide 25. The amide 25 is cyclized by treatment with a Lewis acid, e.g., aluminum chloride, in an inert solvent such as nitrobenzene yielding lactam 26. The amide carbonyl portion of 26 is removed by reduction with lithium aluminum hydride in an ether solvent such as diethyl ether yielding cyclic amine 27. The dye intermediate 27 is isolated by neutralization of the aluminum salts with a strong acid such as HCl, and extraction into an organic solvent such as methylene dichloride. Note that the substituent R in Scheme 6 is selected here the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Compound 30. Compound 30 may be prepared in 3 steps from aminonaphthol 24 as shown in Scheme 6 below. Aminonaphthol 24 is acylated on the nitrogen with 2-bromo-2-methyl propanoyl chloride in pyridine, yielding amide 28. The amid 28 is cyclized by treatment with a Lewis acid such as aluminum chloride in an inert solvent such as nitrobenzene yielding lactam 29. The amide carbonyl portion of 29 is removed by reduction with lithium aluminum hydride in an ether solvent such as diethyl ether yielding cyclic amine 30. The dye intermediate 30 is isolated by neutralization of the aluminum salts with a strong acid such as HCl, and extraction into an organic solvent such as methylene dichloride.

Scheme 6

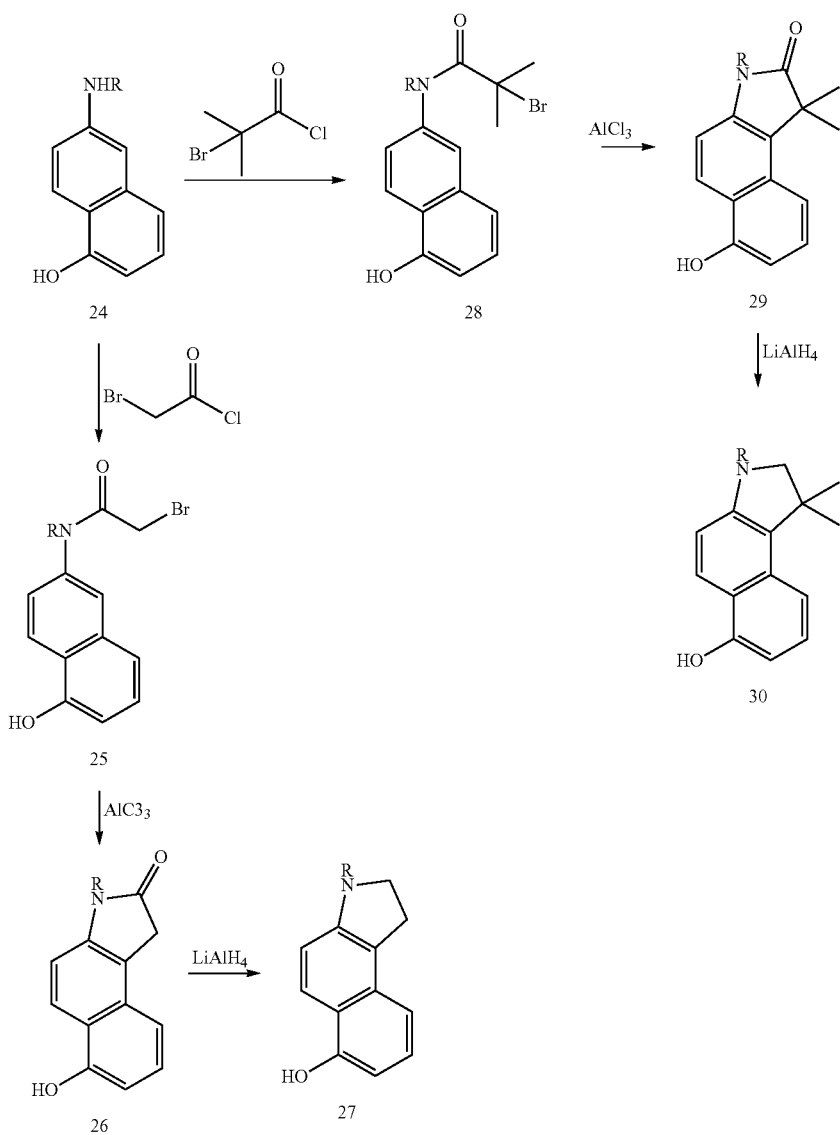

Compound 39. Compound 39 may be prepared in 14 steps from substituted naphthalene 11 as shown below in Scheme 7. Triflate 11 is converted to an aldehyde by displacing the triflate group with carbon monoxide in the presence of hydrogen gas using a palladium catalyst in a solvent inert to hydrogenation, e.g., methanol. The aldehyde is reduced to an alcohol with a hydride reducing agent, e.g., lithium aluminum hydride, in an ether solvent, or, sodium borohydride in an alcohol solvent, e.g., ethanol. The alcohol is converted to the bromide 31 by reaction with HBr in water. Compound 31 is reacted with 2-sodium-dimethyl malonate in a solvent that will solublize the malonate sodium salt without exchanging the sodium cation, e.g., methanol, to yield malonate derivative 32. The methyl esters of 32 are hydrolyzed to di-carboxylates with sodium hydroxide in methanol, and the di-acid is obtained after neutralization with a strong acid such as HCl. The diacid is decarboxylated at elevated temperature to yield acetic acid derivative 33. The carboxylic acid 33 is converted to its acid chloride with oxalyl chloride in an inert solvent such as methylene dichloride. The acid chloride is isolated by removal of the solvent and the excess oxalyl chloride by evaporation, and is converted to the amide 34 by reaction with an amine in an inert solvent such as methylene dichloride. The methyl group on 34 is removed with aqueous HBr to yield the phenol 35. Compound 35 is then converted to triflate 36 with trifluoromethane sulfonyl chloride in pyridine. Removal of the amide hydrogen with sodium hydride, followed by displacement of the triflate with the amide anion catalyzed with palladium as in scheme 5 yields lactam 37. The amide carbonyl portion of 37 is removed by reduction with lithium aluminum hydride in an ether solvent such as diethyl ether yielding cyclic amine 38. The nitro group on 38 is reduced to a primary amino group by reduction with palladium catalyst and hydrogen gas in a solvent that isn't subject to hydrogenation such as methanol. The primary amino group is converted to its diazonium salt with nitrous acid in water, and the diazo group is displaced with hyroxide by treatment with aqueous sodium hydroxide to yield the amino hydroxyl naphthyl dye intermediate 39. The intermediate 39 is isolated by neutralization of the reaction mixture with a strong acid, such as HCl, and extraction of 39 from the aqueous mixture into an organic solvent, such as methylene dichloride. Note that the substituent R in Scheme 7 is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

Compound 43. Nitro lactam 37 in Scheme 7 is converted to its imidate ester 40 by reaction with trimethyl oxonium tetrafluoroborate in methylene chloride. The methoxy group of the imidate ester is then displaced with a methyl group using methyl lithium in toluene to yield the gem-dimethyl cyclic amine 41. The nitro group on 41 is reduced to a primary amino group by reduction with palladium and hydrogen gas in a solvent that isn't subject to hydrogenation such as methanol; the primary amino group is then converted to its diazonium salt with nitrous acid in water to yield 42, and the diazo group is displaced with hydroxide by treatment with aqueous sodium hydroxide to yield the amino hydroxyl naphthyl dye intermediate 43. The intermediate 43 is isolated by neutralization of the reaction mixture with a strong acid, such as HCl, and extraction of 43 from the aqueous mixture into an organic solvent, such as methylene dichloride.

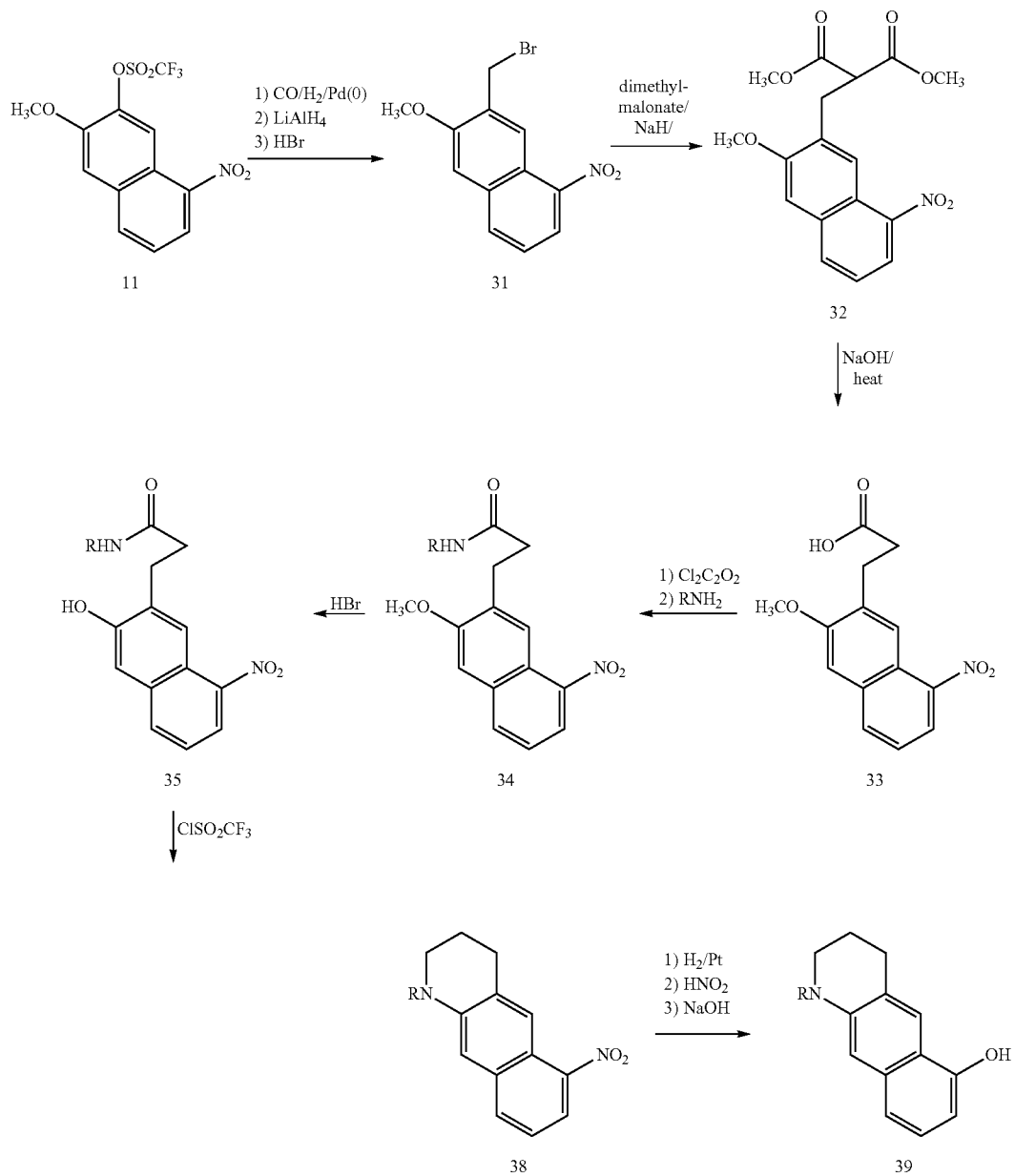

Scheme 7

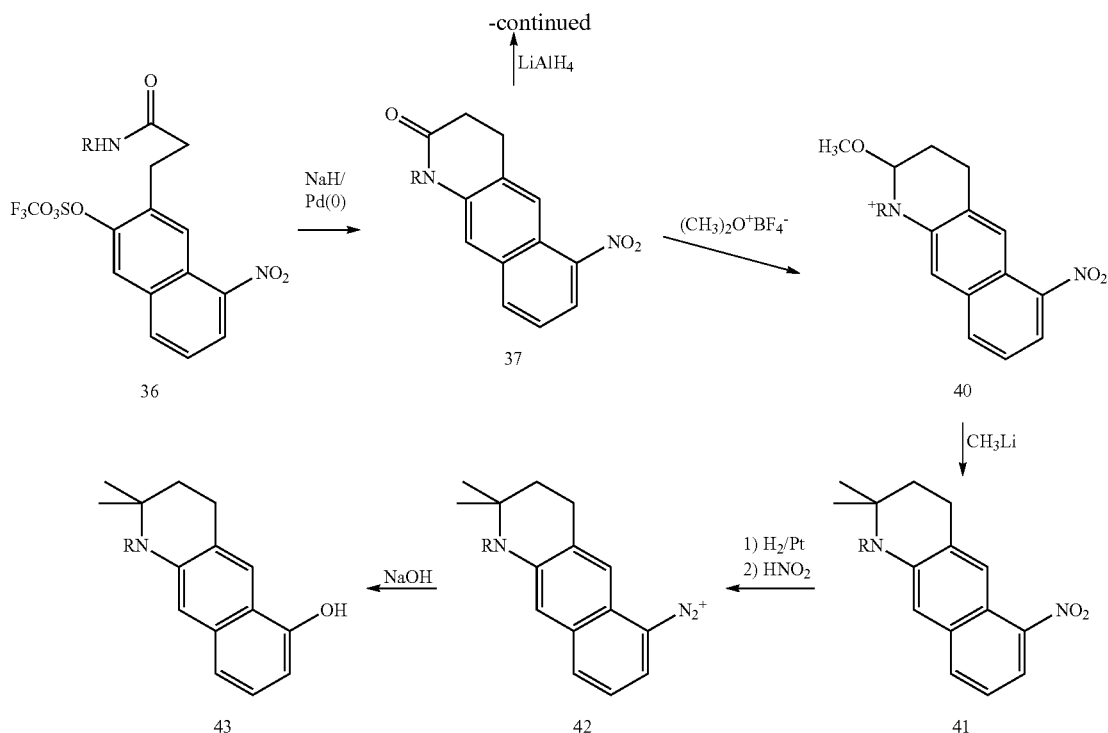

Compound 46. Compound 46 may be prepared in 3 steps from aminophenol 24 as shown in Scheme 8 below. Aminonaphthol 24 is acylated on the nitrogen with 3-chloropropanoyl chloride in pyridine, yielding amide 44. The amide 44 is cyclized by treatment with a Lewis acid such as aluminum chloride in an inert solvent such as nitrobenzene yielding lactam 45. The amide carbonyl portion of 45 is removed by reduction with lithium aluminum hydride in an ether solvent such as diethyl ether yielding cyclic amine 46. The dye intermediate 46 is isolated by neutralization of the aluminum slats with a strong acid such as HCl, and extraction into an organic solvent such as methylene dichloride. Note that the substituent R in Scheme 8 is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independent substituted with one or more $Z_1$.

Compound 48. Compound 48 may be prepared in 2 steps from lactam 45 as shown below in Scheme 8. Lactam 45 in Scheme 8 is converted to its imidate ester 47 by reaction with trimethyloxonium tetrafluoroborate in methylene chloride. The methoxy group of the imidate ester is then displaced with a methyl group using methyl lithium in toluene to yield the gem-dimethyl cyclic amine 48. The dye intermediate 48 is isolated by neutralization of the lithium salts with a strong acid such as HCl, and extraction into an organic solvent such as methylene dichloride.

Scheme 8

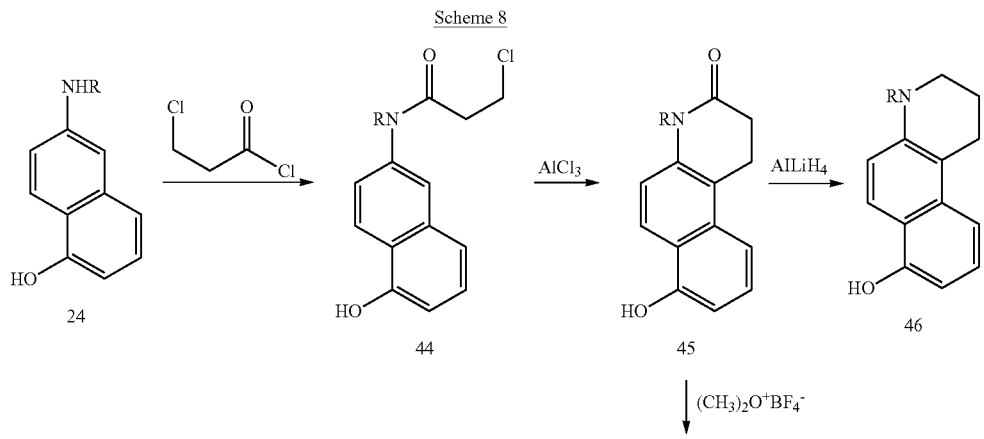

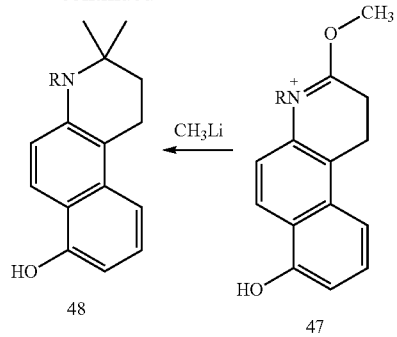

Compounds 51 and 54. As shown in scheme 9, starting with intermediate 30, a bi-cyclic structure 51 with two 5-membered rings can be synthesized in 3 steps. Aminonaphthol 30 is acylated on the nitrogen with 2-bromoacetyl chloride in pyridine, yielding amide 49. The amide 49 is cyclized by treatment with a Lewis acid such as aluminum chloride in an inert solvent such as nitrobenzene yielding lactam 50. The amide carbonyl portion of 45 is removed by reduction with lithium aluminum hydride in an ether solvent such as diethyl ether yielding cyclic amine 51. The dye intermediate 51 is isolated by neutralization of the aluminum slats with a strong acid such as HCl, and extraction into an organic solvent such as methylene dichloride. Note that the substituent R in Scheme 9 is selected from the group consisting of —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$.

As shown in scheme 9, a bi-cyclic structure 54 with both a 5- and a 6-membered ring may be prepared from 30 in three steps. Aminonaphthol 30 is acylated on the nitrogen with 3-chloropropanoyl chloride in pyridine, yielding amide 52. The amide 52 is cyclized by treatment with a Lewis acid such as aluminum chloride in an inert solvent such as nitrobenzene yielding lactam 54. The amide carbonyl portion of 54 is removed by reduction with lithium aluminum hydride in an ether solvent such as diethyl ether yielding cyclic amine 51. The dye intermediate 51 is isolated by neutralization of the aluminum salts with a strong acid such as HCl, and extraction into an organic solvent such as methylene dichloride.

Scheme 9

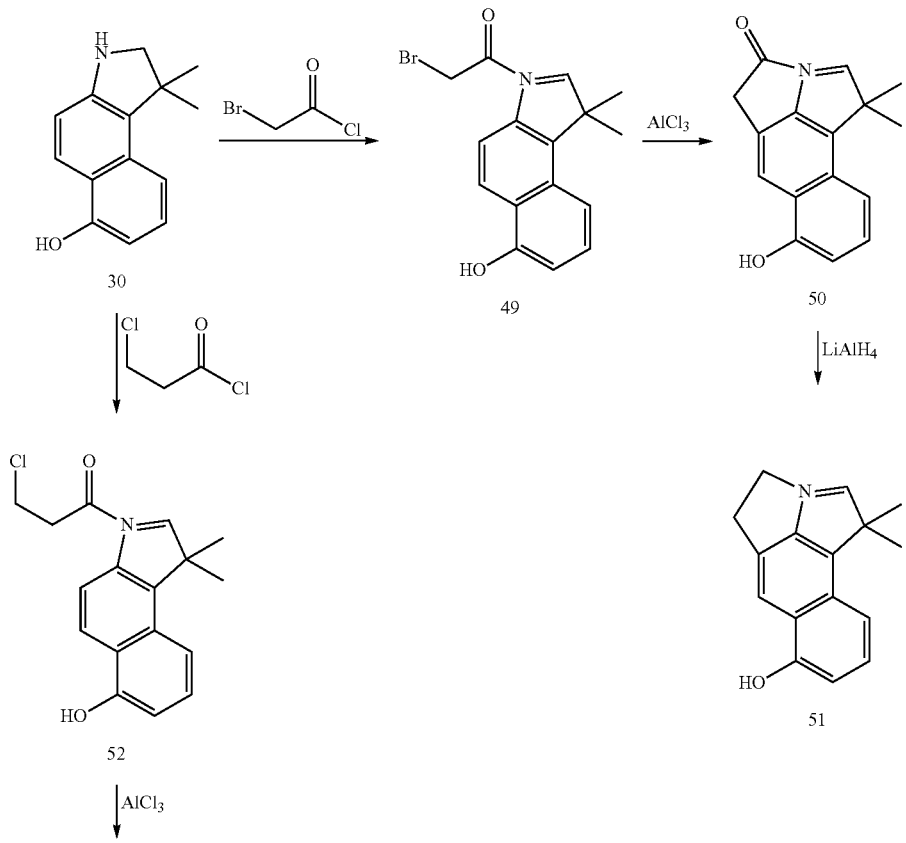

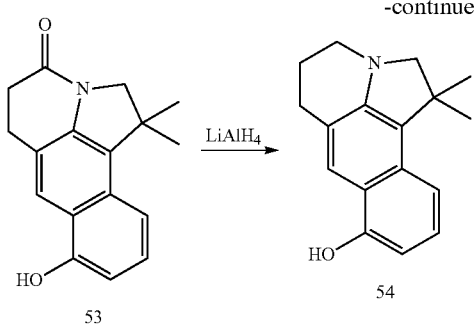

Compounds 57 and 60. As shown in scheme 10, starting with intermediate 48, a bi-cyclic structure 57 with a 5-membered ring and a 6-membered ring can be synthesized in 3 steps. Aminonaphthol 48 is acylated on the nitrogen with 2-bromoacetyl chloride in pyridine, yielding amide 55. The amide 55 is cyclized by treatment with a Lewis acid such as aluminum chloride in an inert solvent such as nitrobenzene yielding lactam 56. The amide carbonyl portion of 56 is removed by reduction with lithium aluminum hydride in an ether solvent such as diethyl ether yielding cyclic amine 57. The dye intermediate 57 is isolated by neutralization of the aluminum salts with a strong acid such as HCl, and extraction into an organic solvent such as methylene dichloride.

As shown in scheme 10, a bi-cycle structure 60 with two 6-membered rings may be prepared from 48 in three steps. Aminonaphthol 48 is acylated on the nitrogen with 3-chloropropanoyl chloride in pyridine, yielding amide 58. The amide 58 is cyclized by treatment with a Lewis acid such as aluminum chloride in an inert solvent such as nitrobenzene yielding lactam 59. The amide carbonyl portion of 59 is removed by reduction with lithium aluminum hydride in an ether solvent such as diethyl ether yielding cyclic amine 60. The dye intermediate 60 is isolated by neutralization of the aluminum salts with a strong acid such as HCl, and extraction into an organic solvent such as methylene dichloride.

Scheme 10

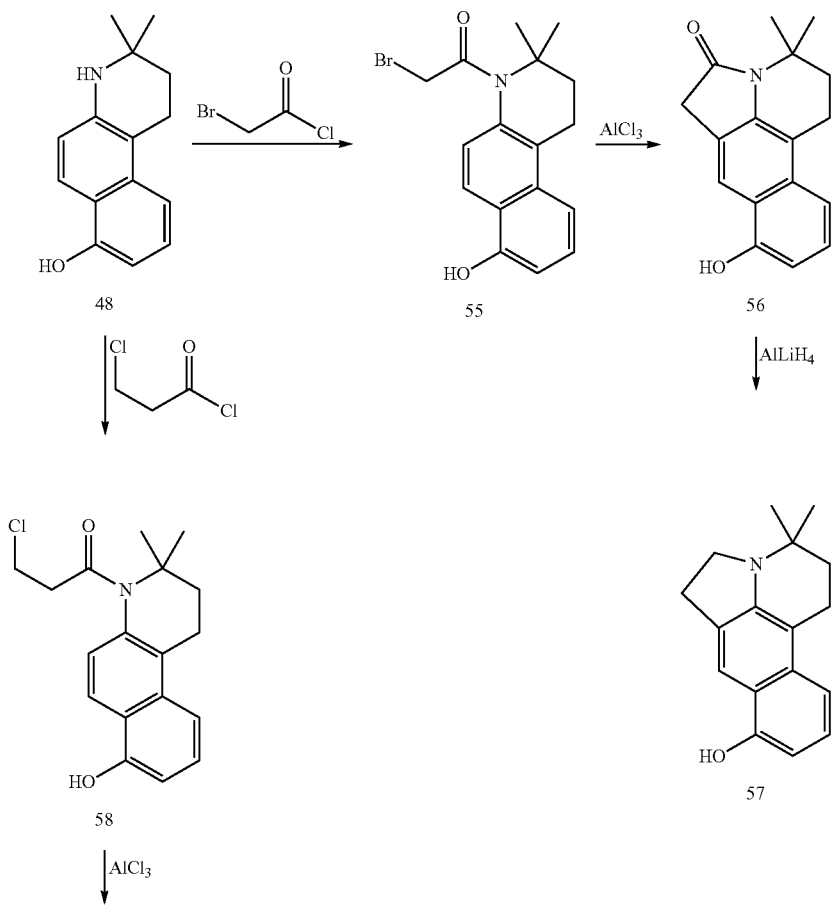

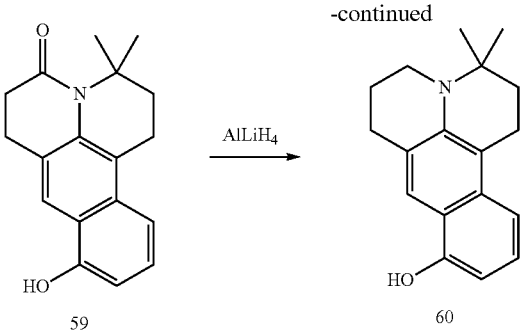

V. Conjugates of Extended Rhodamine Dye Compounds

A. Dye-Conjugate Linking Chemistry. Dyes of the invention may optionally possess a linking group comprising at least one group —$L_1$—$R_x$, where $R_x$ is a reactive group that is attached to the dye D by a covalent linkage $L_1$. In certain embodiments $L_1$ comprises multiple intervening atoms that serve as a spacer, while in other embodiments $L_1$ is simply a bond linking $R_x$ to the dye. Dyes having a linking group may be reacted with a wide variety of organic or inorganic substances Sc that contain or are modified to contain functional groups with suitable reactivity, i.e., a complementary functionality —$L_2$-$R_y$. In certain embodiments $L_2$ comprises multiple intervening atoms that serve as a spacer, while in other embodiments $L_2$ is simply a bond linking $R_y$ to the substance Sc. Reaction of the linking group and the complementary functionality results in chemical attachment of the dye to the conjugated substance Sc, represented by D-L-Sc, where L is the linkage formed by the reaction of the linking group and the complementary functionality.

One of $R_y$ or $R_x$ typically comprise an electrophile, while the other typically comprises a nucleophile, such that the reaction of the electrophile and nucleophile generate a covalent linkage between the dye and the conjugated substance.

Alternatively, one of $R_y$ or $R_x$ typically comprise a photoactivatable group, and becomes chemically reactive only after illumination with light of an appropriate wavelength.

Selected examples of electrophiles and nucleophile that are useful in linking groups and complementary functionalities are shown in Table 2, where the reaction of an electrophilic group and a nucleophilic group yields a covalent linkage.

TABLE 1

Examples Of Some Routes To Useful Covalent Linkages

| Electrophilic Group | Nucleophilic Group | Resulting Covalent Linkage |
| --- | --- | --- |
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |

TABLE 1-continued

Examples Of Some Routes To Useful Covalent Linkages

| Electrophilic Group | Nucleophilic Group | Resulting Covalent Linkage |
| --- | --- | --- |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amineslanilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. oxysuccinimidyl (—ONC$_4$H$_4$O$_2$) oxysulfosuccinimidyl (—ONC$_4$H$_3$ O$_2$—SO$_3$H), 1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates.

The covalent linkage L binds the dye to the conjugated substance Sc either directly (i.e., L is a single bond) or through a combination of stable chemical bonds. For example L may be alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$.

The group —$R_x$ is preferably bound to the dye via the linker $L_1$ at $R_1$, $R_4$-$R_{11}$, or $Y_1$-$Y_4$. More preferably, the linking group —L—$R_x$ is bound to the dye at $R_8$, or $Y_1$-$Y_4$. In a particularly preferred embodiment, the linking group —L—$R_x$ is bound to the dye at $R_8$.

The selection of the linking group used to attach the dye to the conjugated substance typically depends on the complementary functionality on the substance to be conjugated. The types of complementary functionalities typically present on the conjugated substances Sc include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g., amines, thiols, alcohols, phenols), as is typical for proteins. A conjugated substance may be conjugated to more than one dye, which may be the same or different, or to a substance that is additionally modified by a hapten. Although some selectivity can be obtained by careful control of the reaction conditions, selectivity of labeling is best obtained by selection of an appropriate reactive dye.

B. Dye Conjugates

A variety of dye-conjugates may be prepared using the dyes of the invention, such conjugates having the general structure D-L-Sc where D is an extended rhodamine dye of the present invention, L is a covalent linkage, and Sc is a conjugated substance. Dye conjugates of the invention include conjugates of antigens, steroids, vitamins, drugs, haptens, metabolites, toxins, environmental pollutants, amino acids, peptides, proteins, nucleic acids, nucleic acid polymers, carbohydrates, lipids, and polymers. In another embodiment, the conjugated substance is a polysaccharide, nucleotide, oligonucleotide, phospholipid, lipoprotein, lipopolysaccharide, liposome, lipophilic polymer, polymeric microparticle, biological cell or virus. In one aspect of the invention, the conjugated substance is labeled with a plurality of dyes of the present invention, which may be the same or different.

The most preferred conjugated substances are conjugates of haptens, nucleotides, oligonucleotides, nucleic acid polymers, proteins, or polysaccharides. Most preferably, the conjugated substance is nucleic acid, or a substance that interacts in a specific fashion with nucleic acids, such as DNA-binding proteins.

In one embodiment, the conjugated substance Sc is an amino acid (including those that are protected or are substituted by phosphates, carbohydrates, or $C_1$ to $C_{22}$ carboxylic acids), or is a polymer of amino acids such as a peptide or protein. Preferred conjugates of peptides contain at least five amino acids, more preferably 5 to 36 amino acids. preferred peptides include, but are not limited to, neuropeptides, cytokines, toxins, protease substrates, and protein kinase substrates. Also preferred are peptides that serve as organelle localization peptides, that is, peptides that serve to target the conjugated dye for localization within a particular cellular substructure by cellular transport mechanisms. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the conjugated protein is an antibody, an antibody fragment, avidin, streptavidin, a toxin, a lectin, or a growth factor. Preferred haptens include biotin, digoxigenin and fluorophores.

In another embodiment, the conjugated substance Sc is a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). Preferred polysaccharide conjugates are dextran or FICOLL conjugates.

In another embodiment, the conjugated substance Sc, is a lip (typically having 6-25 carbons), including glycolipids, phospholipids, and sphingolipids. Alternatively, the conjugated substance is a lipid vesicle, such as a lipsome, or is a lipoprotein (see below). Some lipophilic substituents are useful for facilitating transport of the conjugated dye into cells or cellular organelles.

In yet another embodiment, the conjugates are dye-conjugates of polymers, polymeric particles, polymeric microparticles including magnetic and non-magnetic microspheres, polymeric membranes, conducting and non-conducting metals and non-metals, and glass and plastic surfaces and particles.

In another embodiment, the conjugated substance Sc, is a member of a specific binding pair that may be used for the detection of an analyte. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Representative specific binding pairs are shown in Table 3.

TABLE 3

Representative Specific Binding Pairs

| antigen | antibody |
|---|---|
| biotin | avidin (or streptavidin or anti-biotin) |
| Igg* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | aDNA (aRNA)** |
| hormone | hormone receptor |
| ion | chelator |

*IgG is an immunoglobulin.
**aDNA and aRNA are the antisense (complementary) strands used for hybridization.

A particularly preferred class of conjugated substances comprise nucleosides/tides that incorporate the dyes of the invention. Such nucleoside/tides conjugates are particularly useful in the context of labeling polynucleotides formed by enzymatic synthesis, e.g., nucleotide triphosphates used in the context of PCR amplification. Sanger-type polynucleotide sequencing, and nick-translation reactions.

Generally, the structure of the labeled nucleoside/tide reagent is

NUC is a nucleoside/tide or nucleoside/tide analog, D is an extended rhodamine dye compound of the invention, and L is a covalent linkage. Alternatively, the structure of a nucleotide comprising a linking group that has not yet been reacted with a complementary functionality is given by the structure

where $R_x$ and $L_1$ are defined above.

Preferably, when NUC includes a purine base, the linkage between NUC and D is attached to the $N^8$-position of the purine, and when NUC includes a 7-deazapurine base, the linkage is attached to the $N^7$-position of the 7-deazapurine, and when NUC includes a pyrimidine base, the linkage is attached to the $N^5$-position of the pyrimidine.

Nucleoside/tide labeling can be accomplished using any one of a large number of known nucleoside/tide labeling techniques employing known linkages, linking groups, and associated complementary functionalities as described above. Generally, the linkage linking the dye and nucleoside should (i) not interfere with oligonucleotide-target hybridization, (ii) be compatible with relevant enzymes, e.g., polymerase, ligases, and the like, and (iii) not adversely affect the fluorescence properties of the dye. Exemplary nucleoside/tide labeling procedures suitable for use in connection with the present invention include the following: Gibson et al. *Nucleic Acids Research*, 15:6455-6467 (1987); Gebeyehu et al, *Nucleic Acids Research*, 15: 4513-4535 (1987); Haralambidis et al. *Nucleic Acids Research*, 15: 4856-4876 (1987); Nelson et al., *Nucleosides and Nucleotides*, 5(3): 233-241 (1986); Bergstrom, et al., *JACS*, 111: 374-375 (1989); and U.S. Pat. Nos. 4,855,225, 5,231,191, and 5,449,767.

In a particularly preferred embodiment, the linkage L linking the dye and nucleoside/tide is an acetylenic, amido or alkenic amido linkage, the linkage between the dye and the nucleoside/tide being formed by reacting an activated N-hydroxysuccinimide (NHS) ester of the dye with an alkynylamino- or alkenylamino-derivatized base of a nucleoside/tide. More preferably, the resulting linkage is 3-(carboxy)amino-1-propyn-1-yl having the structure

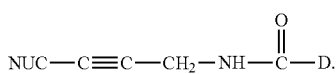

Alternative preferred linkages include substituted propargylethoxyamido linkages having the structure

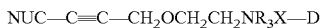

wherein X is selected from the group consisting of

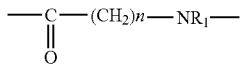

where n ranges from 1 to 5,

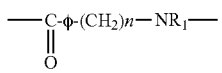

wherein ranges from 1 to 5,

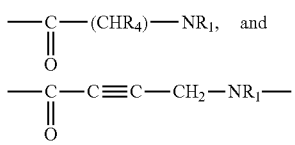

$R_1$ is selected from the group consisting of —H, lower alkyl and protecting group; and $R_3$ is selected from the group consisting of —H and lower alkyl. See Khan et al., U.S. Pat. No. 5,770,716.

The synthesis of alkynylamino-derivatized nucleosides is taught by Hobbs et al. in European Patent Application No. 87305844.0, and Hobbs et al., *J. Org. Chem.*, 54: 3420 (1989). Briefly, the alkynylamino-derivatized nucleotides are formed by placing the appropriate halodideoxynucleoside (usually 5-iodopyrimidine and 7-iodo-7-deazapurine dideoxynucleosides as taught by Hobbs et al. (cited above)) and Cu(I) in a flask, flushing with argon to remove air, adding dry DMF, followed by addition of an alkynylamine, triethylamine and Pd(0). The reaction mixture is stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

Particularly preferred nucleoside/tides of the present invention are shown below wherein

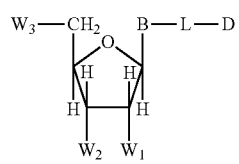

B is a nucleoside/tide base, e.g., uracil, cytosine, deazaadenine, or deazaguarosine: $W_1$ and $W_2$ taken separately are —OH or a group capable of blocking polymerase-mediated template-directed polymerization, e.g., —H, fluorine and the like; $W_3$ is OH, or mono-, di- or triphosphate or phosphate analog: D is a dye compound of the present invention; and L is a covalent linkage linking the dye and the nucleoside/tide. In one particularly preferred embodiment, the nucleotides of the present invention are dideoxynucleotide triphosphate terminators having the structure shown below, including associated counterions if present.

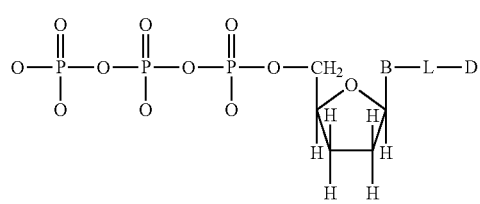

Labeled dideoxy nucleotides such as that shown above find particular application as chain terminating agents in Sanger-type DNA sequencing methods utilizing fluorescent detection.

In another particularly preferred embodiment, the nucleotide of the present invention are deoxynucleotide triphosphates having the structure shown below.

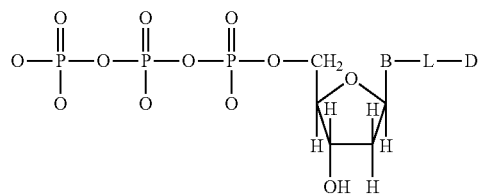

Labeled deoxynucleotides such as that shown in above find particular application as reagents for labeling polymerase extension products, e.g., in the polymerase chain reaction or nick-translation.

In yet another particularly preferred embodiment, the conjugated substance Sc comprise polynucleotides labeled with the dyes of the invention. Such labeled polynucleotides are useful in a number of important contexts including as DNA sequencing primers, PCR primers, oligonucleotides hybridization probes, oligonucleotides ligation probes, and the like.

In one preferred embodiment, the labeled polynucleotide of the present invention include multiple dyes located such that fluorescence energy transfer takes place between a donor dye and an acceptor dye. Such multi-dye energy-transfer polynucleotides find application as spectrally-tunable sequencing primers, e.g., Ju et al., *Proc. Natl. Acad. Sci. USA* 92: 4347-4351 (1995), and as hybridization probes, e.g., Lee et al. *Nucleic Acids Research,* 21: 3761-3766 (1993).

Labeled polynucleotides may be synthesized either enzymatically, e.g., using a DNA polymerase or ligase, e.g., Stryer, *Biochemistry*, Chapter 24, W. H. Freeman and Company (1981), or by chemical synthesis, e.g., by the phosphoramidite method, the phosphite-triester method, and the like, e.g., Gait, *Oligonucleotide Synthesis*, IRL Press (1990). Labels may be introduced during enzymatic synthesis utilizing labeled nucleotide triphosphate monomers as described above, or introduced during chemical synthesis using labeled non-nucleotide or nucleotide phosphoramidites as described above, or may be introduced subsequent to synthesis.

Generally, if the labeled polynucleotide is made using enzymatic synthesis, the following procedure may be used. A template DNA is denatured and an oligonucleotide primer is annealed to the template DNA. A mixture of deoxynucleotide triphosphates is added to the mixture including dGTP, dATP, dCTP, and dTTP where at least a fraction of the deoxynucleotides is labeled with a dye compound of the invention as described above. Next, a polymerase enzyme is added under conditions, where the polymerase enzyme is active. A labeled polynucleotide is formed by the incorporation of the labeled deoxynucleotides during polymerase-mediated strand synthesis. In an alternative enzymatic synthesis method, two primers are used instead of one, one primer complementary to the + strand and the other complementary to the − strand of the target, the polymerase is a thermostable polymerase, and the reaction temperature is cycled between a denaturation temperature and an extension temperature, thereby exponentially synthesizing a labeled complement to the target sequence by PCR, e.g., *PCR Protocols*, Innis et al. eds. Academic Press (1990).

Labeled polynucleotides may be chemically synthesized using the phosphoramidite method. Detailed descriptions of the chemistry used to form polynucleotides by the phosphoramidite method are provided elsewhere, e.g., Caruthers, et al. U.S. Pat. Nos. 4,458,066 and 4,415,732; Caruthers et al., *Genetic Engineering*, 4: 1-17 (1982); *Users Manual Model 392 and 394 Polynucleotide Synthesizers*, pages 6-1 through 6-22, Applied Biosystems, Part No. 901237 (1991). The phosphoramidite method of polynucleotide synthesis is the preferred method because of its efficient and rapid coupling and the stability of the starting materials. The synthesis is performed with the growing polynucleotide chain attached to a solid support, so that excess reagents, which are in the liquid phase, can be easily removed by filtration, thereby eliminating the need for purification steps between synthesis cycles.

The following briefly described the steps of a typical polynucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and the hydroxyl protecting groups on the dyes are removed by treating the polynucleotide solution in base at an elevated temperature, e.g, 55° C.

Any of the phosphoramidite nucleoside monomers may be dye-labeled phosphoramidites as described above. If the 5'-terminal position of the nucleotide is labeled, a labeled non-nucleotidic phosphoramidite of the invention may be used during the final condensation step. If an internal position of the oligonucleotide is labeled, a labeled nucleotidic phosphoramidite of the invention may be used during any of the condensation steps.

Subsequent to synthesis, the polynucleotide may be labeled at a number of positions including the 5'-terminus, e.g., *Oligonucleotides and Analogs*, Eckstein ed., Chapter 8, IRL Press (1991) and Orgel et al., *Nucleic Acids Research* 11(18): 6513 (1983); U.S. Pat. No. 5,118,800; the phosphodiester backbone, e.g., ibid., Chapter 9; or at the 3'-terminus, e.g., Nelson, *Nucleic Acids Research* 20(23): 6253-6259, and U.S. Pat. Nos. 5,401,837 and 5,141,813. For a through review of oligonucleotide labeling procedures see R. Haugland in *Excited States of Biopolymers*, Steiner ed., Plenum Press, N.Y. (1983).

In one preferred post-synthesis chemical labeling method a dye including a carboxy linking group is converted to the N-hydroxysuccinimide ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10-20×) to an aminohexyl derivatized oligonucleotide in 0.25 M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylamine acetate (TEAA). The fraction containing the crude labeled oligonucleotide is further purified by reverse phase HPLC employing gradient elution.

Generally, conjugates typically result from mixing appropriate reactive dyes and the substance to be conjugated in a suitable solvent in which both are soluble, using methods well known in the art, followed by separation of the conjugate from any unreacted dye and by-products. For those reactive dyes that are photoactivated, conjugation requires illumination of the reaction mixture to activate the reactive dye. The dye-conjugate is used in solution or lyophilized and stored for later use.

VI. Applications of Extended Rhodamine Dye Compounds and Extended Rhodamine Dye Conjugates The dyes and conjugates of the present invention are well suited to any method utilizing fluorescent detection, particularly methods requiring the simultaneous detection of multiple spatially-overlapping analytes. Dyes and reagents of the invention are particularly well suited for identifying classes of polynucleotides that have been subjected to a biochemical separation procedure, such as electrophoresis, or that have been distributed among locations in a spatially-addressable nucleic acid hybridization array.

In a preferred category of methods referred to herein as "fragment analysis" or "genetic analysis" methods, labeled polynucleotide fragments are generated through template-directed enzymatic synthesis using labeled primers, probes or nucleotides, e.g., by ligation or polymerase-directed primer extension: the fragments are resolved, by a size-dependent separation process, e.g., electrophoresis or chromatography, or by hybridization to a spatially-addressable nucleic acid hybridization array; and, the resolved fragments are detected subsequent to the separation or hybridization step, e.g., by laser-induced fluorescence. In a particularly preferred embodiment, multiple classes of polynucleotides are resolved simultaneously and the different classes are distinguished by spectrally resolvable labels.

One such fragment analysis method known as amplified fragment length polymorphisim detection (AmpFLP) is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled polynucleotide PCR primer, or by utilizing labeled nucleotide triphosphate in the PCR.

In another such fragment analysis method known as nick translation, an enzymatic polymerization reaction is used to replace unlabeled nucleoside triphosphate in a double-stranded DNA molecule with labeled ones. Free 3'-hydroxyl groups are created within the unlabeled DNA by "nicks" caused by deoxyribonuclease I (DNAase I) treatment. DNA polymerase I then catalyzes the addition of a labeled nucleotide to the 3-hydroxyl terminus of the nick. At the same time, the 5' to 3'-exonuclease activity of this enzyme eliminates the nucleotide unit from the 5'-phosphoryl terminus of the nick. A new nucleotide with a free 3'-OH group is incorporated at the position of the original excised nucleotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on variable number of tandem repeats, or VNTRs. VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2-4 bases) repeated sequence. One of the most abundant interspersed repetitive DNA families in humans is the (dC-dA)n-(dG-dT)n dinucleotide repeat family (also called the (CA)n dinucleotide repeat family). There are thought to be as many as 50,000 to 100,000 (CA)n repeat regions in the human genome, typically with 15-30 repeats per block. Many of these repeat regions are polymorphic in length and can therefore serve as useful genetic markers. Preferably, in VNTR or STR methods, label is introduced into the polynucleotide fragments by using a dye-labeled PCR primer.

In a particularly preferred fragment analysis method, classes identified in accordance with the invention are defined in terms of terminal nucleotides so that a correspondence is established between the four possible terminal bases and the members of a set of spectrally resolvable dyes. Such sets are readily assembled from the dyes of the invention by measuring emission and absorption bandwidths with commercially available spectrophotometers. More preferably, the classes arise in the context of the chemical or chain termination methods of DNA sequencing, and most preferably the classes arise in the context of the chain termination methods, i.e., dideoxy DNA sequencing, or Sanger-type sequencing.

Sanger-type sequencing involves the synthesis of a DNA strand by a DNA polymerase in vitro using a single-stranded or double-stranded DNA template whose sequence is to be determined. Synthesis is initiated at a defined site based on where an oligonucleotide primer anneals to the template. The synthesis reaction is terminated by incorporation of a nucleotide analog that will not support continued DNA elongation, i.e., a terminator. Exemplary terminators include the 2',3'-dideoxynucleoside 5'-triphosphates (ddNTPs) which lack the 3'-OH group necessary for 3' to 5' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP is incorporated. If labeled primers or labeled ddNPTs are used for each reaction, the sequence information can be detected by fluorescence after separation by high-resolution electrophoresis. In the chain termination method, dyes of the invention can be attached to either sequencing primers or dideoxynucleotides. Dyes can be linked to a 5'-end of a primer, e.g., following the teaching in Fung et al, U.S. Pat. No. 4.757,141; on the base of a primer; or on the base of a dideoxynucleotide, e.g. via the alkynylamino linking groups disclosed by Hobbs et al. supra.

Mixtures of labeled polynucleotides may be resolved using an electrophoretic separation process, e.g. Gould and Matthews, cited above: Rickwood and Hames, Eds., *Gel Electrophoresis of Nucleic Acids: A Practical Approach*, IRL Press Limited, London, 1981; Osterman, *Methods of Protein and Nucleic Acid Research*, Vol. 1 Springer-Verlag, Berlin, 1984; or U.S. Pat. Nos. 5,374,527, 5,624,800 and/or 5,552,028. Preferably, the electrophoresis is carried out by capillary electrophoresis, e.g., *Capillary Electrophoresis Theory and Practice*, Grossman and Colburn, eds., Academic Press (1992). Preferably the type of electrophoretic matrix is crosslinked or uncrosslinked polyacrylamide having a concentration (weight to volume)of between about 2-20 weight percent. More preferably, the polyacrylamide concentration is between about 4-8 percent. Preferably in the context of DNA sequencing in particular, the electrophoresis matrix includes a denaturing agent, e.g., urea, formamide, and the like. Detailed procedures for constructing such matrices are given by Maniatis et al., in *Methods in Enzymology*, 65: 299-305

(1980); Maniatis et al., *Biochemistry,* 14: 3787-3794 (1975); Maniatis et al., *Molecular Cloning: A Laboratory Mannual,* Cold Spring Harbor laboratory, New York, pgs. 179-185 (1982); and *ABI PRISM™ 377 DNA Sequence User's Mannual, Rev. A,* Jan. 1995, Chapter 2 (p/n 903433, The Perkin-Elmer Corporation, Foster City, Calif.). The optimal electrophoresis conditions, e.g., polymer concentration, pH, temperature, concentration of denaturing agent, employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations.

Alternatively, mixtures of labeled polynucleotides may be resolved by hybridization to a spatially-addressable nucleic acid hybridization array. Such arrays may be fabricated using any one of a number of different known fabrication techniques. Exemplary fabrication techniques include light-directed in-situ synthesis (e.g., Fodor et al. U.S. Pat. No. 5,744, 305 and related patents) and robotic spotting techniques (e.g., Cheung et al., *Nature Genetics,* 21: 15-19 (1999); Brown et al., U.S. Pat. No. 5,807,522; cantor, U.S. Pat. No. 5,631,134). Where spotting techniques are used, the support-bound capture nucleic acid may range in size from a short oligonucleotide, e.g., 3 to 10 nucleotides in length, to a cDNA fragment, to a whole genome. Methods used to perform the hybridization process are well known and will vary depending upon the nature of the support bound capture nucleic acid and the nucleic acid in solution (e.g., Bowtell, *Nature Genetics,* 21: 25-32 (1999); Brown and Botstein, *Nature Genetics,* 21: 33-37 (1999)).

Subsequent to separation or hybridization, the dye-polynucleotide conjugates are preferably detected by measuring the fluorescence emission from the dye labeled polynucleotides. To perform such detection, the labeled polynucleotides are illuminated by standard means, e.g., high intensity mercury vapor lamps, lasers, or the like. Preferably the illumination means is a laser having an illumination beam at a wavelength above about 600 nm. More preferably, the dye-polynucleotides are illuminated by laser light generated by a He—Ne gas laser or a solid-state diode laser. The fluorescence is then detected by a light-sensitive detector, e.g., a photomultiplier tube, a charged coupled device, or the like. Exemplary detection systems are described elsewhere (e.g., U.S. Pat. Nos. 5,543,026; 5,274,240; 4,879,012; 5,019,652 and 4,811,218; Guo et al., *Nucleic Acids Research,* 22(24): 5456-5465 (1994); Gette and Kreiner, *American Laboratory,* Mar. 1997, pp. 15-17 (1997).

VII. EXAMPLES the invention will be further clarified by a consideration of the following examples, which are intended to be purely exemplary of the invention and not to in any way limit its scope.

Example 1

Synthesis of Compounds 62 and 63 (Scheme 11)

Synthesis of Compound 62. A solution of 6-amino-1-naphthol 61 (8 g, 0.05 mol), iodine (0.5 g, 2 mmol), and acetone (200 mL) was heated at 110° C. (oil bath) for 18 h. The reaction was quenched (aqueous $Na_2$-$S_2O_3$) and extracted with hexane:ethyl acetate (9:1). The organic extract was washed (brine), dried ($Na_2SO_4$ powder), and eluted through a small pack of silica gel. The solvent was evaporated and residue was chromatographed with hexane:ethyl acetate (3:7) to give compound 62 (10.63 g, 88.6%) as yellowish orange solid. $^1$H NMR δ1.28, (s, 6H), 2.38 (s, 3H), 5.26 (s, 1H), 5.40 (s, 1H), 5.58 (s, 1H), 6.54 (t, 1H), 6.74 (dd, 1H), 7.18 (m, 1H), 7.78 (dd, 1H), 7.96 (t, 1H).

Synthesis of Compound 63. A solution of compound 62 (4.82 g, 0.02 mol), Pd/C (10%, 0.5 g), and MeOH (30 mL) was shaken under $H_2$ (60 lbs/in$^2$) in a Parr Hydrogenator for 18 h. After filtration of the reaction mixture, the filtrate was evaporated and the crude residue was chromatographed with hexane:ethyl acetate (3:7) to give compound 63 (4.1 g, 84%) as a pale brown solid. $^1$H NMR δ1.20 (s, 3H), 1.35 (s, 3H), 1.44 (d, 3H), 1.77 (dd, 1H), 2.08 (1H), 3.48 (sept, 1H), 6.54 (d, 1H), 6.73 (d, 1H), 7.23 (t, 1H), 7.38 (d, 1H), 7.87 (d, 1H).

Scheme 11

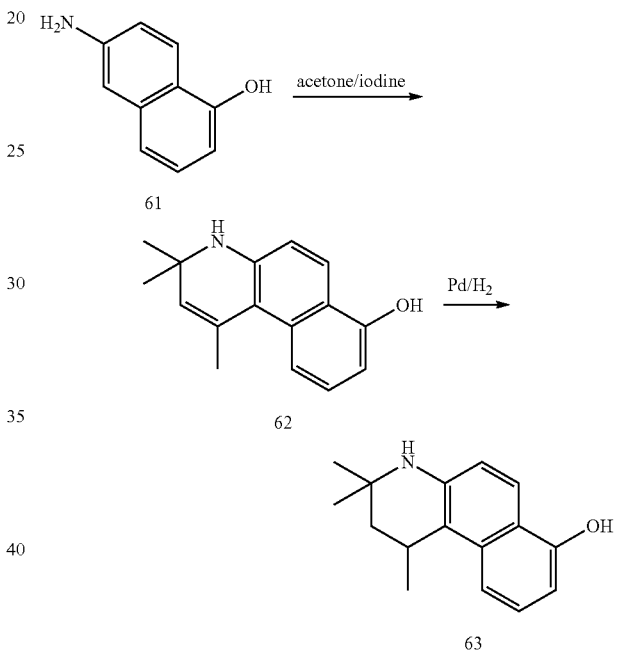

Example 2

Synthesis of Compounds 65, 67 and 69 (Scheme 12)

Synthesis of Dye 65. A solution of compound 63 (0.3209 g, 1.33 mmol), trimellitic anhydride (64) (0.1845 g, 0.96 mmol), and triflic acid (3 mL) was heated at (140-145)° C. under argon for 3 h. The reaction mixture was poured into a solution of brine (150 mL)-$H_2SO_4$ (5%, 10 mL) and was extracted with $CH_2Cl_2$:MeOH (4:1). The organic extract was washed (sat. brine) and then evaporated under reduced pressure. The crude reside was chromatographed with $CH_2Cl_2$:MeOH (from 9:1 to 1:9) to give 65 as two isomers.

Synthesis of Dye 67. A solution of compound 63, dichlorotrimellitic anhydride 66, and triflic acid was reacted and worked up in an identical manner to that described in relation to the synthesis of compound 65. The product dye 67 was isolated as two isomers by chromatography with $CH_2Cl_2$:MeOH.

Synthesis of Dye 69. A solution of compound 63, tricarballylic acid 68, and triflic acid was reacted and worked up in an identical manner to that described in relation to the synthesis of compound 65. The product dye 69 was isolated by chromatography with $CH_2Cl_2$:MeOH.

All publications and patent application cited in this disclosure are hereby incorporated by reference to the same extent as if each individual publication or patent application was specifically and individually indicated to be incorporated by reference.

Although only a few embodiments have been described in detail above, those having ordinary skill in the chemical arts

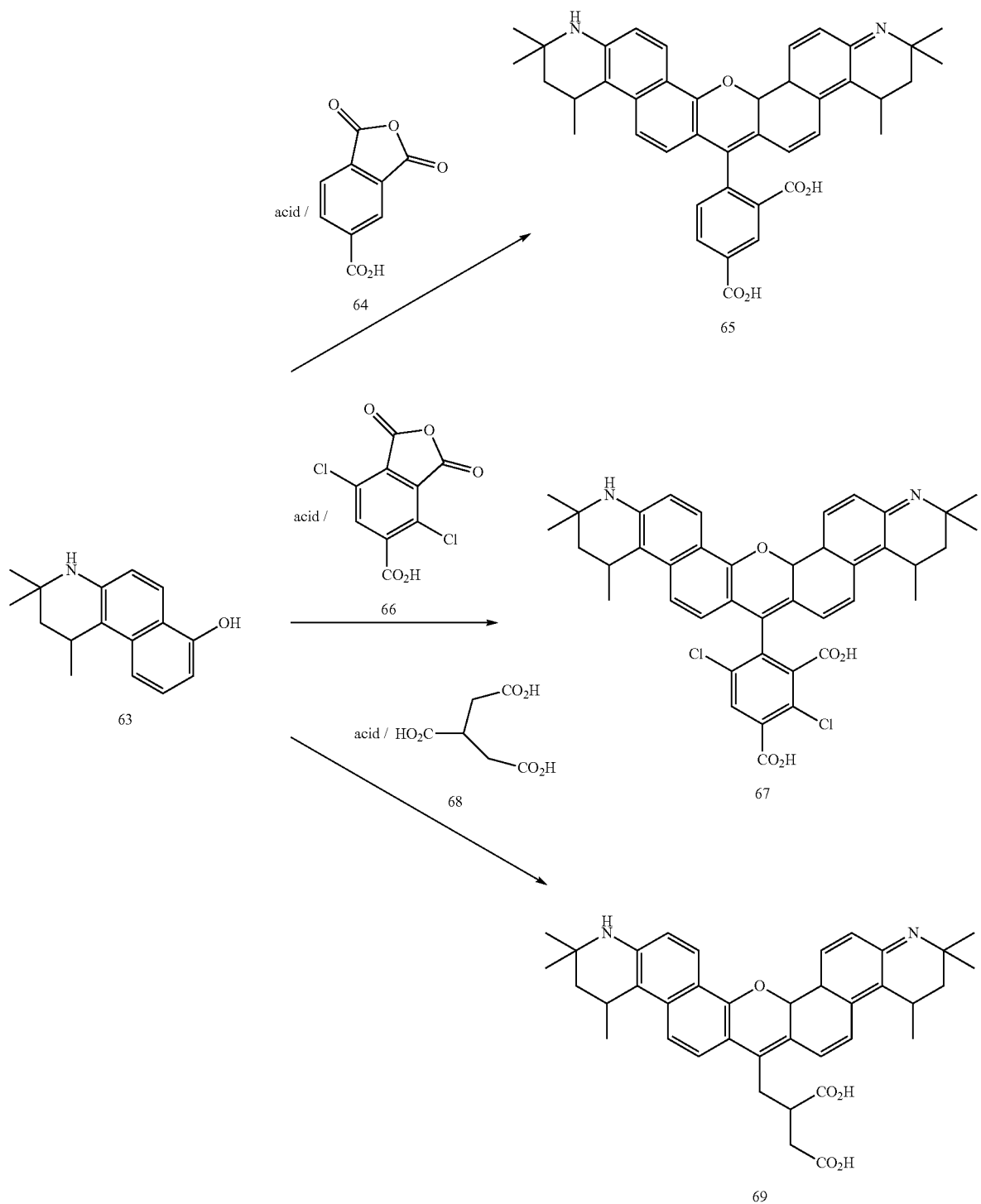

Scheme 12

We claim:
1. A method of polynucleotide sequencing comprising the steps of:
forming a mixture of a first, a second, a third, and a fourth class of polynucleotides such that:
each polynucleotide in the first class includes a 3'-terminal dideoxyadenosine labeled with a first dye;
each polynucleotide in the second class includes a 3'-terminal dideoxycytidine and is labeled with a second dye;
each polynucleotide in the third class includes a 3'-terminal dideoxyguanosine and is labeled with a third dye; and
each polynucleotide in the fourth class includes a 3'-terminal dideoxythymidine and is labeled with a fourth dye;
wherein one of the first, second, third or fourth dyes is an extended rhodamine dye having a structure of one of the following formulae:

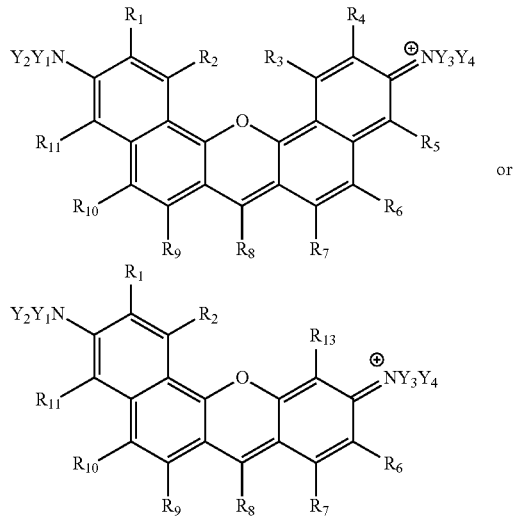

wherein
$R_1, R_2, R_3, R_4, R_5, R_6, R_7, R_9, R_{10}, R_{11}$, and $R_{13}$ when taken alone are selected from —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NR$_2$, —NR$_3$, —NC(O)R, —C(O)R, —C(O)NR$_2$, —CN, and —OR; or
$R_1$ taken together with $R_2$, $Y_1$, or $Y_2$; or
$R_4$ taken together with $R_3$, $Y_3$, or $Y_4$; or
$R_5$ taken together with $R_6$, $Y_3$, or $Y_4$; or
$R_6$ taken together with $R_7$, $Y_3$, or $Y_4$; or
$R_{10}$ taken together with $R_9$ or $R_{11}$; or
$R_{11}$ taken together with $Y_1$, or $Y_2$; or
$R_{13}$ taken together with $Y_3$ or $Y_4$ are selected from alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$;

$R_8$ is selected from —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$;

$Y_1, Y_2, Y_3, Y_4$ when taken alone are selected from —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$; or
$Y_1$ taken together with $R_1$, $R_{11}$ or $Y_2$; or
$Y_2$ taken together with $R_1$, $R_{11}$ or $Y_1$; or
$Y_3$ taken together with $R_4$, $R_5$, $R_6$, $R_{13}$ or $Y_4$; or
$Y_4$ taken together with $R_4$, $R_5$, $R_6$, $R_{13}$ or $Y_3$ are selected from alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$;

$Z_1$ is selected from —R, halogen, —OS(O)$_2$OR, —SO$_2$OR, —SO$_2$R, —SO$_2$NR, —S(O)R, —OP(O)O$_2$RR, —P(O)O$_2$RR, —CO$_2$R, —NR$_2$, —NR$_3$, —NC(O)R, —C(O)R, —C(O)NR$_2$, —CN, —O and —OR, wherein R is independently selected from —H, alkyl, heteroalkyl, aryl, heteroaryl, arylalkyl, heteroarylalkyl and linkage to the polynucleotide; and R is independently selected from —H, alkyl, heteroalkyl, aryl, heteroaryl, arylalkyl, heteroarylalkyl and a linkage to the labeled polynucleotide wherein the linkage is attached to the extended rhodamine compound at $R_1, R_4, R_5, R_6, R_7, R_8, R_9, R_{10}, Y_1, Y_2, Y_3,$ or $Y_4$; and wherein each of the other of the four dyes is spectrally resolvable from the extended rhodamine dye and from each other;
electrophoretically separating the labeled polynucleotides thereby forming bands of similarly sized polynucleotides;
illuminating the bands with an illumination beam capable of causing the dyes to fluoresce; and
identifying the classes of the labeled polynucleotides in the bands by the fluorescence spectrum of the dyes.

2. The method of claim 1, wherein the extended rhodamine dye is configured to be excited by an excitation light source having a wavelength greater than about 630 nm.

3. The method of claim 1, wherein the one or more labeled polynucleotides is labeled at a nucleobase of the polynucleotide, and further wherein:
(a) when the nucleobase comprises a purine base, the linking group connecting the extended rhodamine dye to the nucleobase is attached to the 8-position of the purine base;
(b) when the nucleobase comprises a 7-deazapurine base, the linking group connecting the extended rhodamine dye to the nucleobase is attached to the 7-position of the 7-deazapurine base; and
(c) when the nucleobase comprises a pyrimidine base, the linking group connecting the extended rhodamine dye to the nucleobase is attached to the 5-position of the pyrimidine base.

4. The method of claim 1, wherein the linking group connecting the extended rhodamine dye to a nucleobase of the one or more labeled polynucleotide is attached to $R_8$ of the extended rhodamine dye.

5. The method of claim 1, wherein the linking group connecting the extended rhodamine dye to the labeled polynucleotide is an alkynylamino- derivatized or alkenyl-derivatized linkage.

6. The method of claim 1, wherein the one or more labeled polynucleotides has a structure of one of the following formulae:

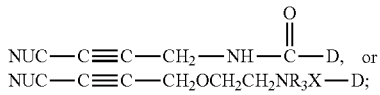

wherein NUC is a nucleobase of the one or more labeled polynucleotides;
D is the extended rhodamine dye;
$R_3$ is selected from the group consisting of —H and lower alkyl;
X is selected from one of the following formulae:

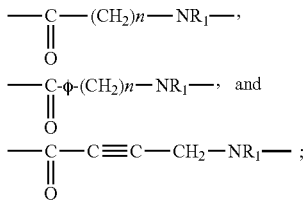

n is an integer of 1 to 5; and
$R_1$ is —H, lower alkyl, or protecting group.

7. A method for sequencing a nucleic acid sequence comprising:
forming a mixture of extended labeled primers by hybridizing a nucleic acid sequence with a fluorescently labeled oligonucleotide primer in the presence of deoxynucleotide triphosphates, at least one dideoxynucleotide triphosphate and a DNA polymerase, the DNA polymerase extending the primer with the deoxynucleotide triphosphates until a dideoxynucleotide triphosphate is incorporated which terminates extension of the primer;
separating the mixture of extended primers; and
determining the sequence of the nucleic acid sequence by fluorescently measuring the mixture of extended primers formed;
wherein the fluorescently labeled oligonucleotide primer comprises an extended rhodamine dye having a structure of the formula:

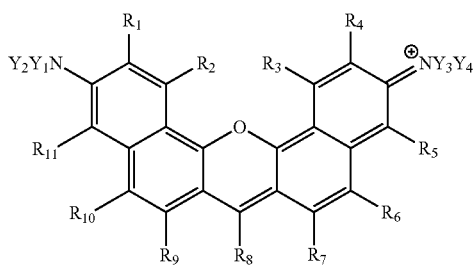

or

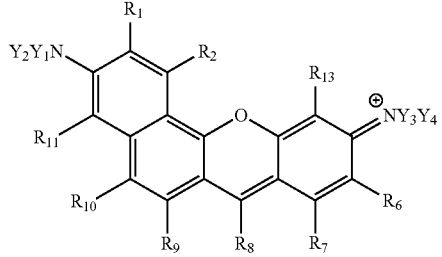

wherein
$R_1, R_2, R_3, R_4, R_5, R_6, R_7, R_9, R_{10}, R_{11}$, and $R_{13}$ when taken alone are selected from —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, heteroarylalkyl independently substituted with one or more $Z_1$, halogen, —OS(O)$_2$OR, —S(O)$_2$OR, —S(O)$_2$R, —S(O)$_2$NR, —S(O)R, —OP(O)O$_2$RR, —P(O)O$_2$RR, —C(O)OR, —NR$_2$, —NR$_3$, —NC(O)R, —C(O)R, —C(O)NR$_2$, —CN, and —OR; or
$R_1$ taken together with $R_2$, $Y_1$, or $Y_2$; or
$R_4$ taken together with $R_3$, $Y_3$, or $Y_4$; or
$R_5$ taken together with $R_6$, $Y_3$, or $Y_4$; or
$R_6$ taken together with $R_7$, $Y_3$, or $Y_4$; or
$R_{10}$ taken together with $R_9$ or $R_{11}$; or
$R_{11}$ taken together with $Y_1$, or $Y_2$; or
$R_{13}$ taken together with $Y_3$ or $Y_4$ are selected from alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$;
$R_8$ is selected from —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$;
$Y_1, Y_2, Y_3, Y_4$ when taken alone are selected from —H, alkyl, alkyl independently substituted with one or more $Z_1$, heteroalkyl, heteroalkyl independently substituted with one or more $Z_1$, aryl, aryl independently substituted with one or more $Z_1$, heteroaryl, heteroaryl independently substituted with one or more $Z_1$, arylalkyl, arylalkyl independently substituted with one or more $Z_1$, heteroarylalkyl, and heteroarylalkyl independently substituted with one or more $Z_1$; or
$Y_1$ taken together with $R_1$, $R_{11}$ or $Y_2$; or
$Y_2$ taken together with $R_1$, $R_{11}$ or $Y_1$; or
$Y_3$ taken together with $R_4$, $R_5$, $R_6$, $R_{13}$ or $Y_4$; or
$Y_4$ taken together with $R_4$, $R_5$, $R_6$, $R_{13}$ or $Y_3$ are selected from alkyleno, alkyleno independently substituted with one or more $Z_1$, heteroalkyleno, heteroalkyleno independently substituted with one or more $Z_1$, aryleno, aryleno independently substituted with one or more $Z_1$, heteroaryleno, and heteroaryleno independently substituted with one or more $Z_1$;
$Z_1$ is selected from —R, halogen, —OS(O)$_2$OR, —SO$_2$OR, —SO$_2$R, —SO$_2$NR, —S(O)R, —OP(O)

$O_2RR$, $-P(O)O_2RR$, $-CO_2R$, $-NR_2$, $-NR_3$, $-NC(O)R$, $-C(O)R$, $-C(O)NR_2$, $-CN$, $-O$ and $-OR$, wherein R is independently selected from $-H$, alkyl, heteroalkyl, aryl, heteroaryl, arylalkyl, heteroarylalkyl and linkage to the fluorescently labeled primer; and wherein R is independently selected from $-H$, alkyl, heteroalkyl, aryl, heteroaryl, arylalkyl, heteroarylalkyl and a linkage to the fluorescently labeled primer; wherein the linkage is attached to the extended rhodamine compound at $R_1$, $R_4$, $R_5$, $R_6$, $R_7$, $R_8$, $R_9$, $R_{10}$, $Y_1$, $Y_2$, $Y_3$, or $Y_4$; and wherein linkage is attached to the fluorescently labeled primer at a nucleobase of the primer:

(a) when the nucleobase comprises a purine base, the linkage connecting the extended rhodamine dye to the nucleobase is attached to the 8-position of the purine base;

(b) when the nucleobase comprises a 7-deazapurine base, the linkage connecting the extended rhodamine dye to the nucleobase is attached to the 7-position of the 7-deazapurine base; and (c) when the nucleobase comprises a pyrimidine base, the linkage connecting the extended rhodamine dye to the nucleobase is attached to the 5-position of the pyrimidine base.

8. The method of claim 7, wherein the extended rhodamine dye is configured to be excited by an excitation light source having a wavelength greater than about 630 nm.

9. The method of claim 7, wherein the linking group connecting the extended rhodamine dye to a nucleobase of the fluorescently labeled primer is attached to $R_8$ of the extended rhodamine dye.

10. The method of claim 7, wherein the linking group connecting the extended rhodamine dye to the fluorescently labeled primer is an alkynylamino- derivatized or alkenyl-derivatized linkage.

11. The method of claim 7, wherein the fluorescently labeled primer has a structure of one of the following formulae:

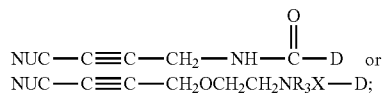

wherein NUC is a nucleobase of the fluorescently labeled primer;

D is the extended rhodamine dye;

$R_3$ is selected from the group consisting of $-H$ and lower alkyl;

X is selected from one of the following formulae:

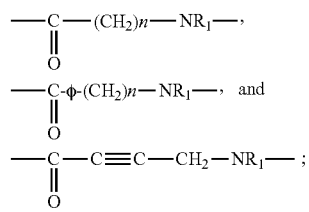

n is an integer of 1 to 5; and $R_1$ is $-H$, lower alkyl, or protecting group.

12. The method of claim 7, wherein the separating step is an electrophoretic size-dependent separation process.

* * * * *